(12) United States Patent
Wing et al.

(10) Patent No.: US 8,211,012 B2
(45) Date of Patent: Jul. 3, 2012

(54) TISSUE RETRACTOR SYSTEM

(75) Inventors: Charles Wing, Center Valley, PA (US);
William J. Beutler, Mechanicsburg, PA (US); Walter J. McMurray, Saint Johns, FL (US); Donald A. Buss, Macungie, PA (US); James David Hughett, Liberty Township, OH (US); Jeffrey S. Tompkins, Quakertown, PA (US); Jeffrey Cole, Macungie, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 931 days.

(21) Appl. No.: 12/241,897

(22) Filed: Sep. 30, 2008

(65) Prior Publication Data

US 2010/0081885 A1    Apr. 1, 2010

(51) Int. Cl.
*A61B 1/32* (2006.01)
(52) U.S. Cl. .................... 600/215; 600/233; 600/210
(58) Field of Classification Search .......... 600/210–216, 600/219, 220, 224, 228, 229, 231–233
See application file for complete search history.

(56) References Cited

U.S. PATENT DOCUMENTS

| | | | |
|---|---|---|---|
| 569,839 | A | 10/1896 | Burgin |
| 2,670,731 | A | 3/1954 | Carl |
| 2,693,795 | A | 11/1954 | Grieshaber |
| 2,751,903 | A | 6/1956 | Ivory |
| 2,812,759 | A | 11/1957 | Taylor |
| 3,384,077 | A | 5/1968 | Gauthier |
| 3,509,873 | A | 5/1970 | Karlin |
| 3,724,449 | A | 4/1973 | Gauthier |
| 3,747,592 | A | 7/1973 | Santos |
| 4,263,899 | A | 4/1981 | Burgin |
| 4,502,485 | A | 3/1985 | Burgin |
| 4,510,926 | A | 4/1985 | Inaba |
| 4,852,552 | A | 8/1989 | Chaux |
| 4,896,661 | A | 1/1990 | Bogert |
| 4,989,587 | A | 2/1991 | Farley |
| 5,052,373 | A | 10/1991 | Michelson |
| RE34,150 | E | 12/1992 | Santilli |
| 5,400,774 | A | 3/1995 | Villalta |

(Continued)

FOREIGN PATENT DOCUMENTS

DE        197 08 587        11/1998

(Continued)

OTHER PUBLICATIONS

H. Michael Myer, MD, Aesculap Spine, miaspas mini TTA, Microsurgical Anterior, 2007, pp. 1-27.

(Continued)

*Primary Examiner* — Eduardo C Robert
*Assistant Examiner* — Stuart S Bray
(74) *Attorney, Agent, or Firm* — RatnerPrestia

(57) ABSTRACT

A tissue retractor system includes first and second arms extending from a support assembly, and third and fourth arms extending from a support mechanism. Each arm includes a proximal span, a distal span, and a blade support between the proximal span and distal span. The retractor system features retractor units that can be used independently or in a nested arrangement. The system also includes instruments for inserting a spinal rod. A method for implanting a spinal rod through an incision includes the steps of inserting the spinal rod through a dividable tube, turning the rod subcutaneously toward a rod receiving anchor and advancing the rod subcutaneously toward the rod receiving anchor.

18 Claims, 27 Drawing Sheets

U.S. PATENT DOCUMENTS

| | | | |
|---|---|---|---|
| 5,616,117 A * | 4/1997 | Dinkler et al. | 600/232 |
| 5,667,481 A | 9/1997 | Villalta | |
| 5,728,046 A * | 3/1998 | Mayer et al. | 600/210 |
| 5,772,583 A | 6/1998 | Wright | |
| 5,776,054 A | 7/1998 | Bobra | |
| 5,792,044 A | 8/1998 | Foley et al. | |
| 5,795,291 A | 8/1998 | Koros | |
| 5,928,139 A * | 7/1999 | Koros et al. | 600/205 |
| 5,931,777 A | 8/1999 | Sava | |
| 5,944,658 A | 8/1999 | Koros et al. | |
| 5,954,635 A | 9/1999 | Foley et al. | |
| 5,967,972 A | 10/1999 | Santilli | |
| 5,984,865 A | 11/1999 | Farley | |
| 5,984,867 A | 11/1999 | Deckman | |
| 6,007,487 A | 12/1999 | Foley et al. | |
| 6,139,493 A | 10/2000 | Koros | |
| 6,152,871 A | 11/2000 | Foley et al. | |
| 6,342,036 B1 | 1/2002 | Cooper | |
| 6,416,467 B1 | 7/2002 | McMillin | |
| 6,416,468 B2 | 7/2002 | Deckman | |
| 6,425,859 B1 | 7/2002 | Foley et al. | |
| 6,431,025 B1 | 8/2002 | Koros | |
| 6,485,491 B1 | 11/2002 | Farris et al. | |
| 6,520,907 B1 | 2/2003 | Foley et al. | |
| 6,679,833 B2 | 1/2004 | Smith et al. | |
| 6,837,891 B2 | 1/2005 | Davison et al. | |
| 6,849,064 B2 | 2/2005 | Hamada | |
| 6,869,398 B2 | 3/2005 | Obenchain et al. | |
| 6,979,291 B1 | 12/2005 | Phillips | |
| 7,147,599 B2 | 12/2006 | Phillips | |
| 7,156,805 B2 | 1/2007 | Thalgott et al. | |
| 7,160,300 B2 | 1/2007 | Jackson | |
| 7,182,729 B2 | 2/2007 | Abdelgany et al. | |
| 7,198,598 B2 | 4/2007 | Smith et al. | |
| 7,207,949 B2 | 4/2007 | Miles | |
| 7,250,052 B2 | 7/2007 | Landry et al. | |
| 7,306,603 B2 | 12/2007 | Boehm, Jr. et al. | |
| 7,318,817 B2 | 1/2008 | Hamada | |
| 7,946,982 B2 * | 5/2011 | Hamada | 600/233 |
| 7,976,463 B2 * | 7/2011 | Dewey et al. | 600/210 |
| 8,062,217 B2 * | 11/2011 | Boucher et al. | 600/215 |
| 2003/0191371 A1 | 10/2003 | Smith et al. | |
| 2003/0208203 A1 | 11/2003 | Lim et al. | |
| 2004/0049101 A1 | 3/2004 | Phillips | |
| 2004/0133077 A1 | 7/2004 | Obenchain | |
| 2004/0176665 A1 | 9/2004 | Branch et al. | |
| 2005/0027170 A1 | 2/2005 | Nohara et al. | |
| 2005/0080320 A1 | 4/2005 | Lee et al. | |
| 2005/0113644 A1 | 5/2005 | Obenchain et al. | |
| 2005/0137461 A1 | 6/2005 | Marchek et al. | |
| 2005/0154389 A1 | 7/2005 | Selover et al. | |
| 2005/0159650 A1 | 7/2005 | Raymond et al. | |
| 2005/0159651 A1 | 7/2005 | Raymond et al. | |
| 2005/0215866 A1 | 9/2005 | Kim | |
| 2005/0228380 A1 | 10/2005 | Moore et al. | |
| 2005/0240209 A1 | 10/2005 | Hamada | |
| 2006/0058079 A1 | 3/2006 | Goto | |
| 2006/0135852 A1 | 6/2006 | Koros | |
| 2006/0167454 A1 | 7/2006 | Ludwig et al. | |
| 2006/0167487 A1 | 7/2006 | Hamada | |
| 2006/0178566 A1 | 8/2006 | Fetzer | |
| 2006/0178693 A1 | 8/2006 | Hamada | |
| 2006/0271096 A1 | 11/2006 | Hamada | |
| 2007/0021656 A1 | 1/2007 | Martin | |
| 2007/0038216 A1 | 2/2007 | Hamada | |
| 2007/0055109 A1 | 3/2007 | Bass | |
| 2007/0055110 A1 | 3/2007 | Bass | |
| 2007/0073111 A1 | 3/2007 | Bass | |
| 2007/0073117 A1 * | 3/2007 | Raridan, Jr. | 600/310 |
| 2007/0203399 A1 | 8/2007 | Gephart | |
| 2007/0208227 A1 | 9/2007 | Smith | |
| 2007/0213714 A1 | 9/2007 | Justis et al. | |
| 2007/0233097 A1 | 10/2007 | Anderson et al. | |
| 2007/0233155 A1 | 10/2007 | Lovell | |
| 2007/0282171 A1 | 12/2007 | Karpowicz | |
| 2008/0125788 A1 | 5/2008 | Cohen et al. | |
| 2008/0188718 A1 * | 8/2008 | Spitler et al. | 600/213 |

FOREIGN PATENT DOCUMENTS

| | | |
|---|---|---|
| EP | 0 749 724 A1 | 12/1996 |
| EP | 0 749 724 B1 | 12/1996 |
| EP | 1192905 | 4/2002 |
| WO | WO 03/086202 A2 | 10/2003 |
| WO | WO 03/086202 A3 | 10/2003 |
| WO | WO 2004/002323 A2 | 1/2004 |
| WO | WO 2004/002323 A3 | 1/2004 |
| WO | WO 2006/020982 | 2/2006 |
| WO | WO 2006/074191 | 7/2006 |
| WO | WO 2006/125029 | 11/2006 |
| WO | WO 2007/092056 | 8/2007 |
| WO | WO 2007/149426 | 12/2007 |
| WO | WO 2008/024937 | 2/2008 |
| WO | WO 2008/045719 | 4/2008 |
| WO | WO 2008/063416 | 5/2008 |

OTHER PUBLICATIONS

European Search Report for Application No. EP 09 17 1234; Search Completed Jan. 22, 2010.

* cited by examiner

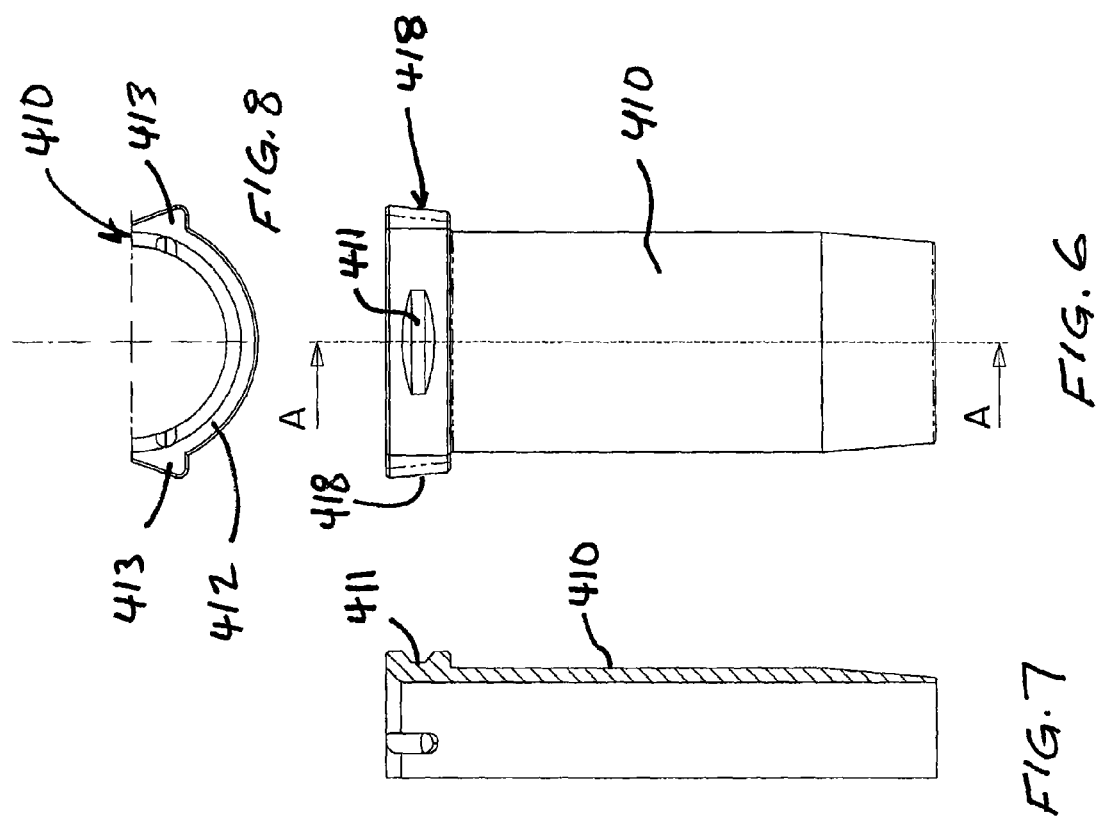

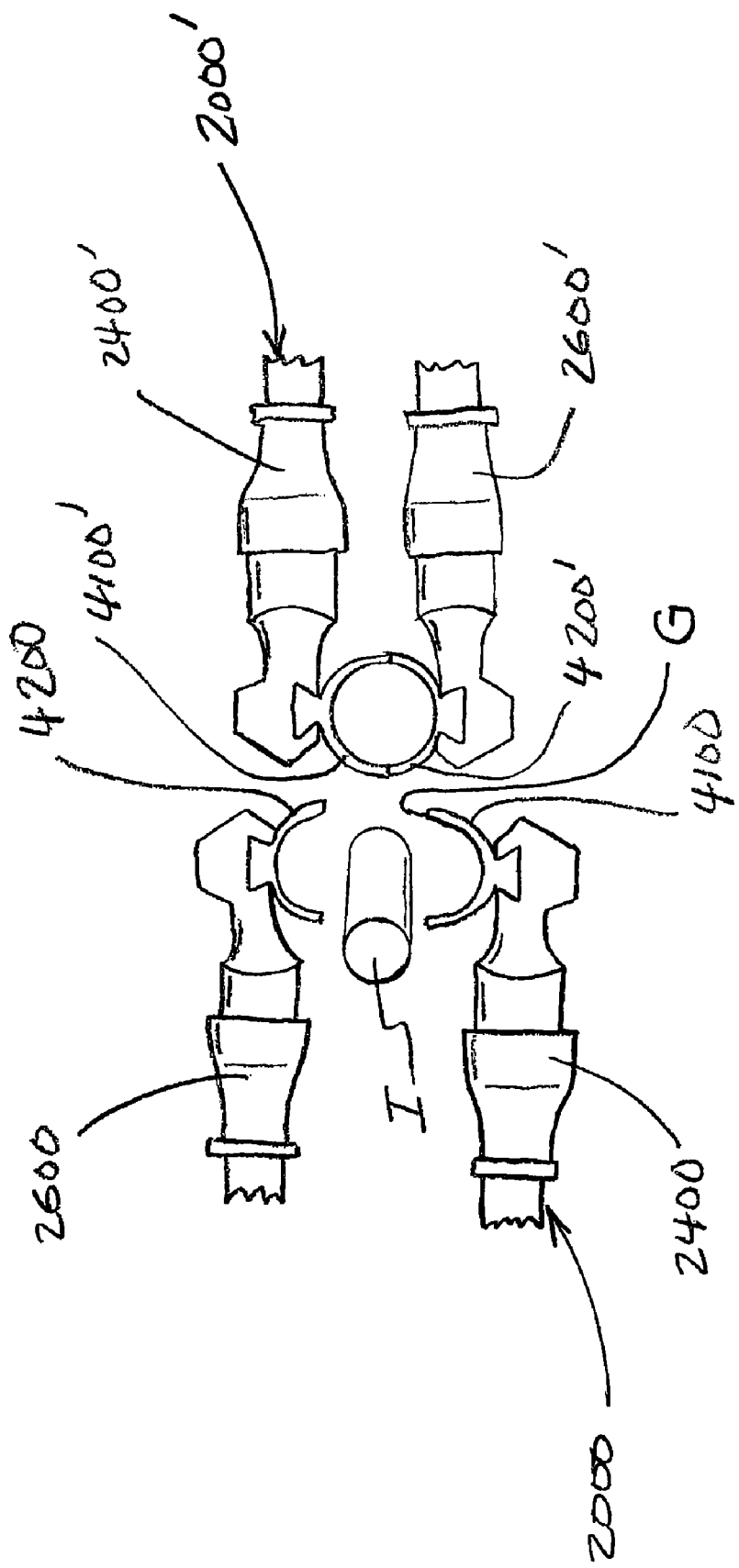

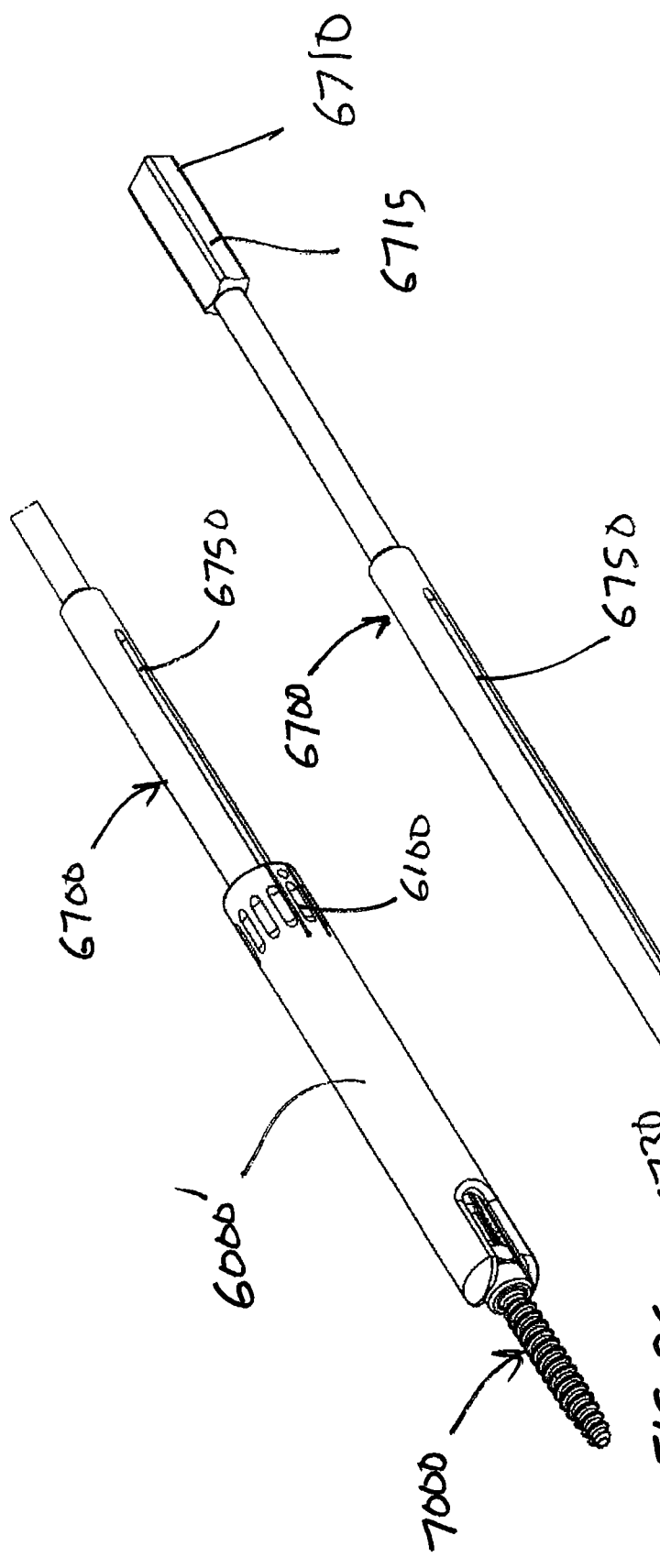
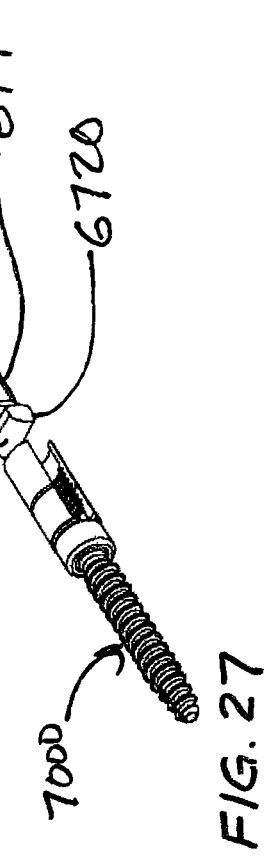
FIG. 26
FIG. 27

TISSUE RETRACTOR SYSTEM

BACKGROUND OF THE INVENTION

In surgical procedures that require incisions, it is desirable to establish a clear and unobstructed view of the operating field. Various instruments are available to hold an incision open and maintain muscles, organs, blood vessels and other tissue out of the field of view. The desire to establish a clear and unobstructed view of the operating field must be balanced with the need to minimize trauma to the patient. Large incisions that strip muscle or damage delicate tissue lead to increased patient trauma, increased risk of complications from surgery and longer recovery times.

A number of retractor assemblies have been developed that hold open incisions, while limiting damage to tissue. These assemblies use long "blades" to hold open incisions. Many retractors are designed to be used in essentially one way, with a fixed arrangement of components. The components often have a limited range of motion, and only work with larger incisions. Moreover, many retractor systems have large levers and other obstructions that limit operability and the ability to neatly arrange the instrumentation over the incision. Often times, this limits the ability to move components smoothly to expand or retract the incision. Furthermore, known systems fail to adequately support the vertical position of the blades in the incision, and keep the blade arms stabilized. Based on all of these drawbacks, known retractor assemblies leave much to be desired in terms of operational flexibility, functionality, adaptability to different procedures, adaptability to different surgeon preferences, and other aspects.

SUMMARY OF THE INVENTION

In a first aspect of the invention, a tissue retractor system for maintaining and adjusting the size of an incision during a minimally invasive surgical procedure includes a single retractor frame or "unit" used alone. The retractor unit includes a first retractor arm, a second retractor arm and a support assembly. The first and second retractor arms extend from the support assembly. The first arm may include a proximal span connected to the support assembly, a distal span and a blade support between the proximal span and the distal span. The second arm may include a proximal span connected to the support assembly, a distal span and a blade support between the proximal span and the distal span. A retractor blade is connected to each of the first and second retractor arms. The first and second retractor arms may include an in-line pivot mechanism that allows the retractor blades to be tilted and locked at different orientations within an incision to spread apart tissue.

In a second aspect of the invention, a tissue retractor system for maintaining and adjusting the size of an incision during a minimally invasive surgical procedure includes a first arm and a second arm that extend from a support assembly. The first arm includes a proximal span connected to the support assembly, a distal span and a blade support between the proximal span and the distal span. The second arm includes a proximal span connected to the support assembly, a distal span and a blade support between the proximal span and the distal span. The tissue retractor system also includes a third arm and a fourth arm extending from a support mechanism. The third arm includes a proximal span connected to the support mechanism, a distal span and a blade support between the proximal span and the distal span. The fourth arm includes a proximal span connected to the support mechanism, a distal span and a blade support between the proximal span and the distal span. The third and fourth arms extend generally perpendicularly to the first and second arms in a nested arrangement, with the third arm resting on top of the distal spans of the first and second arms, and the fourth arm resting on top of the proximal spans of the first and second arms.

In a third aspect of the invention, a tissue retractor system for maintaining and adjusting the size of an incision during a minimally invasive surgical procedure includes a first arm and a second arm extending from a support assembly. The first arm includes a proximal span connected to the support assembly, a distal span, and a blade support between the proximal span and distal span. The second arm includes a proximal span connected to the support assembly, a distal span, and a blade support between the proximal span and distal span. The tissue retractor system also includes a third arm and a fourth arm extending from a support mechanism. The third arm includes a proximal span connected to the support mechanism, a distal span, and a blade support between the proximal span and distal span. The fourth arm includes a proximal span connected to the support mechanism, a distal span, and a blade support between the proximal span and distal span. Each of the proximal spans includes an in-line pivot mechanism, the in-line pivot mechanism including a cylindrical knob that is rotatable about a longitudinal axis of the knob to pivot the arm to which the knob is connected. An internal lock inside the knob fixes the orientation of the arm to which the knob is connected after a rotation of the knob.

In a fourth aspect of the invention, a tissue retractor system for maintaining and adjusting the size of an incision during a minimally invasive surgical procedure includes a retractor arm and a retractor blade. The retractor arm includes a top surface, a bottom surface opposite the top surface, and a slot that extends through the arm between the top surface and the bottom surface. The retractor blade is locked in the slot of the retractor arm by a locking mechanism. At least one of the slot and the retractor blade includes a contoured sidewall. The contoured sidewall allows insertion of the blade into the slot through the top surface of the arm and prevents the blade from completely exiting the slot through the bottom surface of the arm.

In a fifth aspect of the invention, a minimally-invasive learning procedure for inserting a spinal fixation rod is provided which allows a surgeon to gradually increase their proficiency and decrease the size of the incision that they make to insert the rod. In one version, the method includes the step of making a first incision through tissue and a second incision through tissue in proximity to the first incision. A dividable tube is inserted into the first incision. The dividable tube includes a pair of semi-cylindrical blades that form a generally cylindrical tube when mated together. A first rod receiving anchor is inserted through the dividable tube and driven into bone beneath the first incision. A second rod receiving anchor is driven into bone beneath the second incision. For the less experienced surgeon, the dividable tube blades may be spread apart from one another to widen the first incision prior to inserting the rod receiving anchor into the first incision. For the more experienced surgeon, the dividable tube blades may be kept in a closed condition during insertion of the anchor, thereby minimizing the size of the first incision. The spacing between the dividable tube blades, as well as the orientations of the blades, may be adjusted by the surgeon at any time during the procedure. The spacing between the blades is adjustable in small increments anywhere between a fully opened and fully closed condition to suit the surgeon's skill level. A spinal rod having a leading end is inserted through the dividable tube and into the first incision. The blades of the dividable tube may be spread apart at any spacing to provide additional room to manipulate the rod and insertion instrument between the tube blades. Once the spinal rod is inserted through the dividable tube, the spinal rod is turned so that the leading end of the rod is steered through one of the gaps between the blades. The leading end is turned subcutaneously toward the second rod receiving anchor and advanced until the leading end is received by a rod receiving slot in the second rod receiving anchor. The trailing end of the spinal rod is received in a rod receiving slot of the first rod receiving anchor. The spinal rod is then secured to the rod receiving anchors.

BRIEF DESCRIPTION OF THE DRAWINGS

The foregoing summary and the following description will be better understood when reviewed in conjunction with the following exemplary drawing figures, of which:

FIG. 6 is a front view of a retractor blade used with the retractor assembly of FIG. 1;

FIG. 7 is a side cross-section view of the retractor blade of FIG. 6;

FIG. 8 is a top view of the retractor blade of FIG. 6;

FIG. 17 is a truncated top view of the retractor units of FIG. 16 shown in one possible mode of operation;

FIG. 26 is an exploded perspective view of the rod anchor and orientation tool of FIG. 26;

FIG. 27 is a block flow diagram illustrating steps for a minimally invasive method for implanting an elongated spinal rod.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
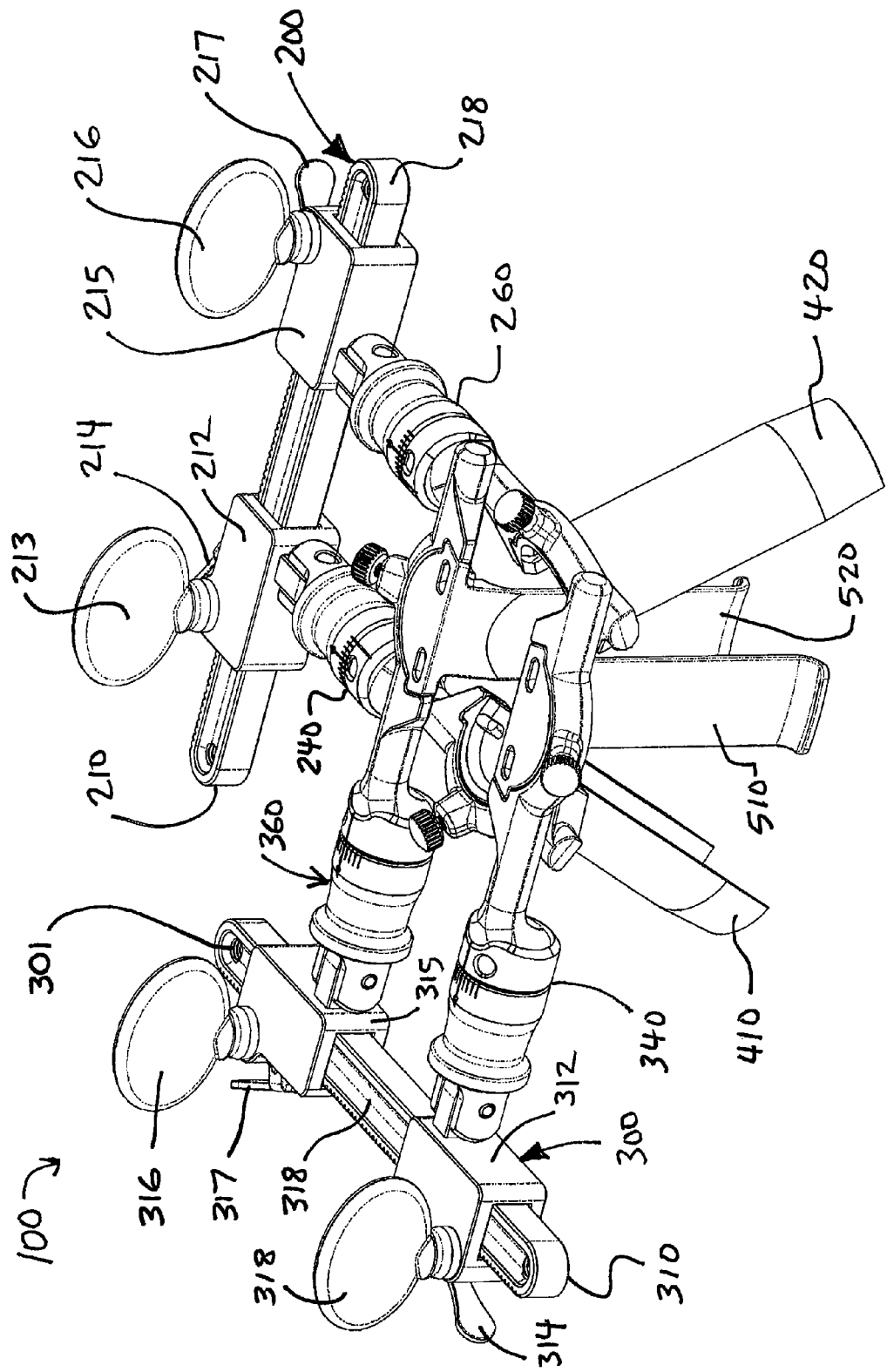
FIG. 1 is a perspective view of a first retractor assembly in accordance with one exemplary embodiment of the invention.

Referring now to FIG. 1, a retractor assembly or "mini-retractor" 100 is shown in accordance with a first exemplary embodiment of the invention. Retractor assembly 100 includes a first retractor unit 200 and a second retractor unit 300 placed on top of the first retractor unit in a stacked or nested arrangement. The pair of retractor units cooperate with one another while working independently to control the size and shape of an incision. As will be explained in more detail below, first retractor unit 200 can be operated by itself within an incision, or accompanied by the second retractor unit 300 if deemed necessary by the surgeon. If operated alone, the first retractor unit 200 can maintain a relatively small incision held open by a pair of tubular blades 410 and 420. If the surgeon desires to increase the size of the incision to better see the operating field, the first retractor blades 410 and 420 can be spread apart, and the second retractor unit 300 added over the top of the first retractor unit 200 in the stacked arrangement shown. When first and second retractor units 200 and 300 are stacked together as shown, the two can be operated in tandem, in a form-fit configuration that allows the second retractor unit to move smoothly over top the first retractor unit, while being fully supported by the first retractor unit.

The option of nesting upper retractor unit 300 over lower retractor unit 200 provides two important functions: (1) it serves as a learning aid for surgeons who begin using the retractors, and (2) it provides operational flexibility for surgeons of all experience levels.

When used as a learning aid, the nested retractor units 200 and 300 allow a surgeon to gradually work toward using a smaller and smaller incision over time. A surgeon with less experience may opt to stack retractor 300 on top of retractor 200 and expand the incision in two directions, so as to provide a larger field of view. With practice, the surgeon may learn to work through smaller and smaller openings between the blades. With additional practice, the surgeon may stop using upper retractor 300 altogether, and expand the incision using only lower retractor 200. With even more practice, the surgeon may learn to minimize the extent to which the blades are spread apart on lower retractor 200. For some procedures, the surgeon can eliminate their need to spread apart the blades altogether. In addition, the surgeon may progress toward using retractor blades and units with smaller openings, such as a percutaneous-type retractor. The present invention contemplates the use of percutaneous-type retractor units, as will be explained below.

With regard to operational flexibility, the nesting arrangement gives the surgeon the option to add the upper retractor 300 during the course of a procedure, and increase the size of the incision if the need arises unexpectedly. For example, a surgeon having experience with the retractor units 200 and 300 may inspect an incision and initially decide that the incision only requires a small amount of expansion in a cranial-caudal direction. The surgeon may choose to only insert lower retractor unit 200 into the incision. During the procedure, the surgeon may discover that the incision requires additional widening in the medial-lateral direction, which cannot be done with lower retractor unit 200. In such a situation, the upper retractor unit 300 can be easily added over top the lower retractor unit to provide the needed expansion in the medial-lateral direction.

First retractor unit 200 includes a first retractor arm 240, a second retractor arm 260 and a support assembly 210 to which the first and second retractor arms are connected. A first retractor blade 410 is connected to first retractor arm 240, and a second retractor blade 420 is connected to second retractor arm 260. First and second retractor blades 410 and 420 are configured for insertion into an incision to hold open the incision, so that a surgeon can access the operating field. In addition, first and second retractor blades 410 and 420 are configured to move toward and away from one another to adjust the width of the incision. For example, retractor blades 410 and 420 may be moved away from one another to increase the width of the incision and spread apart soft tissues so that the surgeon can see the operating field. In this arrangement, retractor blades 410 and 420 form a "dividable tube", the advantages of which will be explained below. Preferably, first and second retractor blades 410 and 420 are positioned to adjust the width of the incision in the cranial-caudal direction. Using mechanisms that will be explained below, the lateral position of each retractor blade is adjustable and lockable, and the orientation of each retractor blade relative to its respective arm is preferably lockable, so as to hold open the incision and underlying tissues in a desired arrangement.

Figure 2:
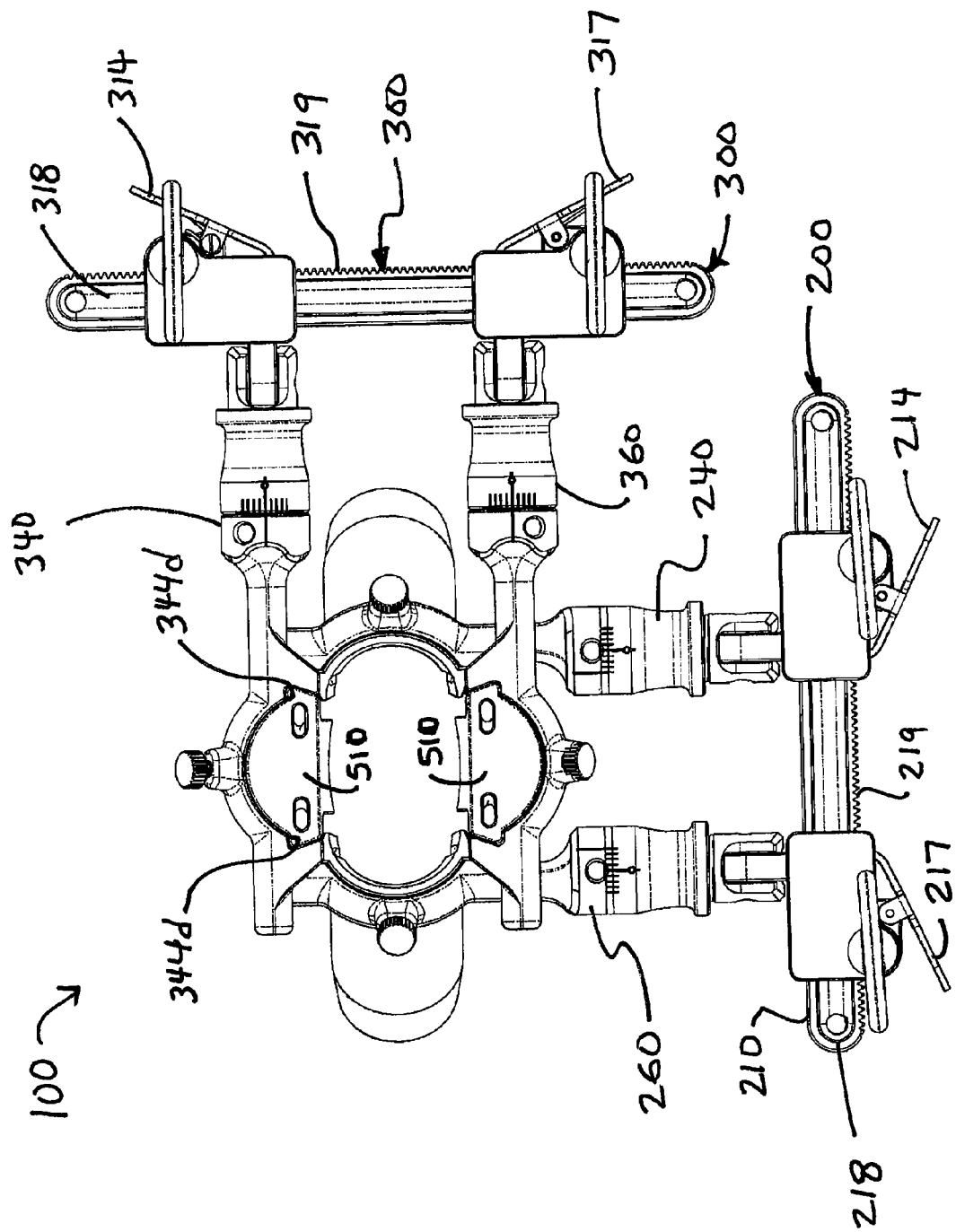
FIG. 2 is a top view of the retractor assembly of FIG. 1.

Blades 410 and 420 are moved in response to lateral displacement of first and second retractor arms 240 and 260, respectively. Referring to FIG. 2, support assembly 210 includes a rack 218 that guides the lateral movement of retractor arms 240 and 260. First retractor arm 240 is connected to rack 218 by a first lateral adjustment assembly 212, and second retractor arm 260 is connected to the rack by a second lateral adjustment assembly 215. A variety of adjustable mechanisms can be used to control movement of the first and second retractor arms 240 and 260. In FIG. 1, lateral adjustment assemblies 212 and 215 include gears 213 and 216 respectively, the gears having handle portions that are more visible in FIG. 1. Gears 213 and 216 engage a series of teeth 219 along an edge of rack 218. In this arrangement, rotation of gear 213 is operable to move first lateral adjustment assembly 212 and first retractor arm 240 along rack 218. Similarly, rotation of gear 216 is operable to move second lateral adjustment assembly 215 and second retractor arm 260 along rack 218. Lateral adjustment assemblies 212 and 215 include spring latches 214 and 217, respectively. Spring latches 214 and 217 are biased by a torsion spring into engagement with teeth 219 to lock the lateral positions of first and second retractor arms 240 and 260. Levers on spring latches 214 and 217 are pivotable against the bias of the torsion springs to move the latches out of engagement with teeth 219 and allow lateral adjustment of first and second retractor arms 240 and 260. First and second retractor blades 410 and 420 are generally semi-cylindrical in cross section. In this configuration, blades 410 and 420 form a generally cylindrical access port when the blades are moved together. The diameter of the generally cylindrical access port can be expanded to provide access for inserting one or more rod anchors into the spine. The access port is also large enough to provide access for inserting a disc replacement, interbody or other implant. The diameter of the port between blades 410 and 420 may be between about 20 mm and about 30 mm. Smaller or larger dimensions may also be used in accordance with the invention. Where more than one screw is inserted between blades 410 and 420, the surgeon may choose to spread the blades apart using the lateral adjustment assembles 212 and 215 to provide enough room to manipulate the screws. The blades may be separated to create any spacing that accommodates the surgeon's skill and experience level. By inserting multiple screws through a single, adjustable incision opening, the amount of disturbance to surrounding soft tissue can be controlled and minimized.

Second retractor unit 300 includes a third retractor arm 340, a fourth retractor arm 360 and a support mechanism 310 to which the third and fourth retractor arms are connected. A third retractor blade 510 is connected to third retractor arm 340, and a fourth retractor blade 520 is connected to fourth retractor arm 360. Like the first and second retractor blades 410 and 420, third and fourth retractor blades 510 and 520 are configured for insertion into an incision to hold open the incision, so that a surgeon can access the operating field. Third and fourth retractor blades 510 and 520 are optional, however, and can be used at the surgeon's discretion to expand an incision. Third and fourth retractor blades 510 and 520 are configured to move toward and away from one another to adjust the width of the incision. For example, retractor blades 510 and 520 may be moved away from one another to increase the width of the incision and spread apart the soft tissues so that the surgeon can see the operating field. Preferably, third and fourth retractor blades 510 and 520 are positioned to adjust the width of the incision in the medial-lateral direction. Using mechanisms that will be explained below, the lateral position of each retractor blade is preferably lockable, and the orientation of each retractor blade relative to its respective arm is preferably lockable, so as to hold open the incision and underlying tissues in a desired arrangement.

Blades 510 and 520 are moved in response to lateral displacement of third and fourth retractor arms 340 and 360, respectively. Support mechanism 310 includes a rack 318 that guides the lateral movement of retractor arms 340 and 360. Third retractor arm 340 is connected to rack 318 by a third lateral adjustment assembly 312, and fourth retractor arm 360 is connected to the rack by a fourth lateral adjustment assembly 315. As with the first and second retractor arms 240 and 260, a variety of adjustable mechanisms can be used to control movement of the third and fourth retractor arms 340 and 360. Lateral adjustment assemblies 312 and 315 include gears 313 and 316 respectively, the gears having handle portions that are more visible in FIG. 1. Gears 313 and 316 engage a series of teeth 319 along an edge of rack 318, and operate in the same manner as gears 213 and 216 to adjust the lateral positions of the third and fourth retractor arms, respectively. Lateral adjustment assemblies 312 and 315 further include spring latches 314 and 317, respectively, to lock the lateral positions of third and fourth retractor arms 340 and 360.

Levers on spring latches 314 and 317 are pivotable against the bias of the torsion springs to move the latches out of engagement with teeth 319 and allow lateral adjustment of third and fourth retractor arms 340 and 360.

First and second retractor arms 240 and 260 are essentially mirror images of one another, with the same components. Similarly, third and fourth retractor arms 340 and 360 are essentially mirror images of one another with the same components, but being distinct from the first and second retractor arms 240 and 260 in a few respects. Therefore, only the features of the first and third retractor arms 240 and 340 will be discussed in the following paragraphs, with the understanding that each feature described on first retractor arm 240 is also present on second retractor arm 260 and labeled with the same reference number plus 20. Moreover, each feature described on third retractor arm 340 is also present on fourth retractor arm 360 and labeled with the same reference number plus 20.

Figure 4:
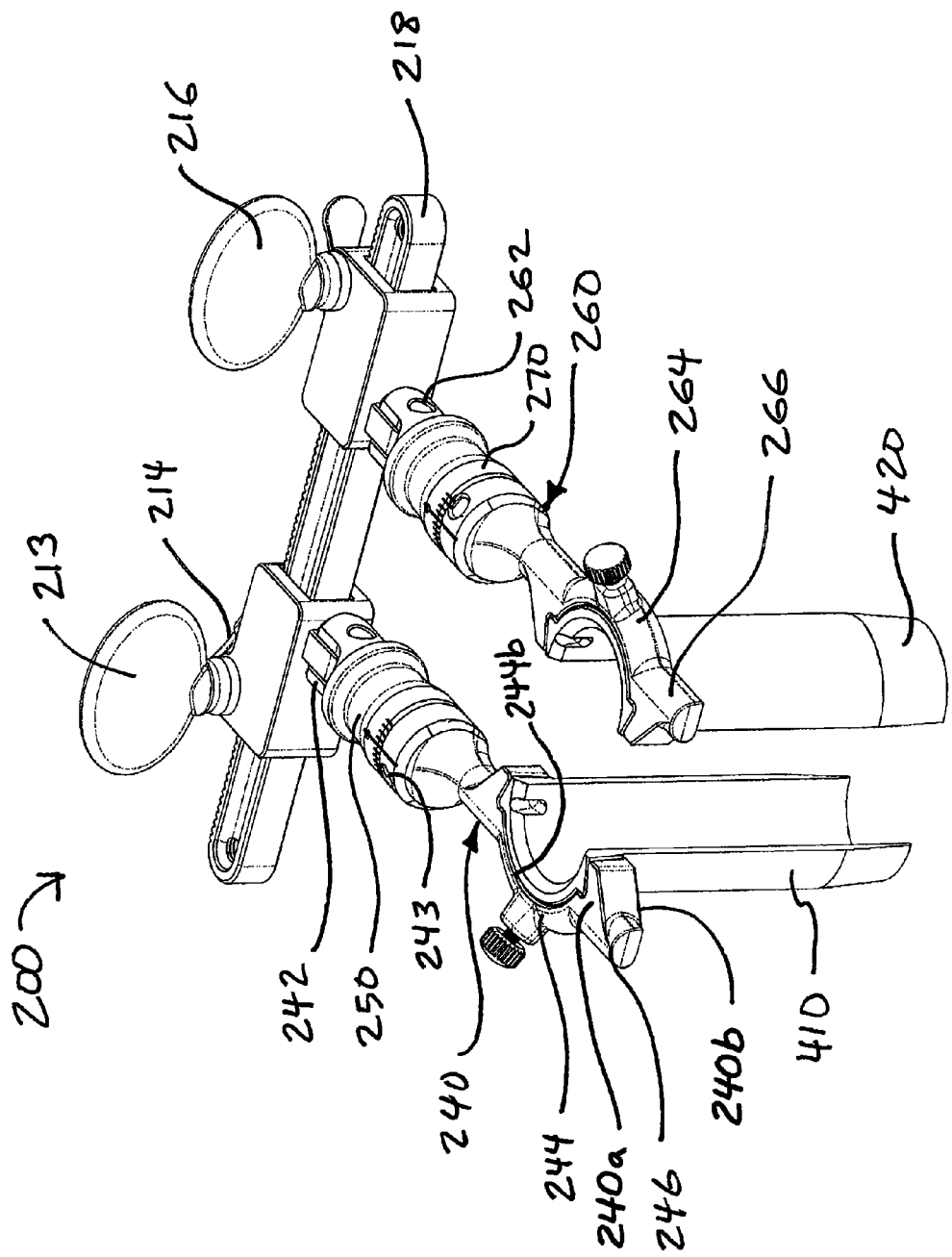
FIG. 4 is a perspective view of a first retractor unit used with the assembly of FIG. 1.

Referring to FIG. 4, first retractor arm 240 includes a proximal span 242 connected to support assembly 200 and a distal span 246. A blade support 244 extends between the proximal and distal spans 242 and 246. Proximal span 242 and distal span 246 each include straight portions that are aligned coaxially with one another. Straight portions each have a rounded upper contour that forms a guide track upon which third and fourth retractor arms 340 and 360 can slide and pivot. The guide track portion is preferably formed of a very hard and smooth anodized material, creating an extremely low friction surface.

Proximal span 242 is connected to first lateral adjustment assembly 212 by a pin connection and hinge. The hinge allows first retractor arm 240 to pivot around the axis of rack 218. The pivot arrangement allows retractor arm 240 to be raised or lowered with respect to the incision so that the vertical orientation of the blade is properly aligned or square with the incision. The hinge also allows for minor adjustment of the arm's position to maintain a flat nested arrangement with the other retractor arms and to allow the retractor unit to sit better on the patient's skin.

Blade support 244 connects first retractor arm 240 to first retractor blade 410. In general, it is desirable to have a connection between the blade and the arm that allows the blade to be dropped or loaded into the arm from above the arm. To this end, blade support 244 of retractor arm 240 has a top-loading configuration that allows blades to be inserted from above the arm. First retractor blade 410 is secured to blade support 244 by a locking screw 244a that extends through a screw hole in the retractor arm. Retractor arm 240 includes a top surface 240a and a bottom surface 240b opposite the top surface. In this context, the phrase "top surface" refers to the surface of the retractor arm that is oriented upwardly and facing the surgeon when the retractor is in use. A rounded slot 244b extends between the top surface 240a and bottom surface 240b. Slot 240b receives first retractor blade 410 and has a geometry that conforms to the cross-sectional shape of the first retractor blade.

Figure 5:
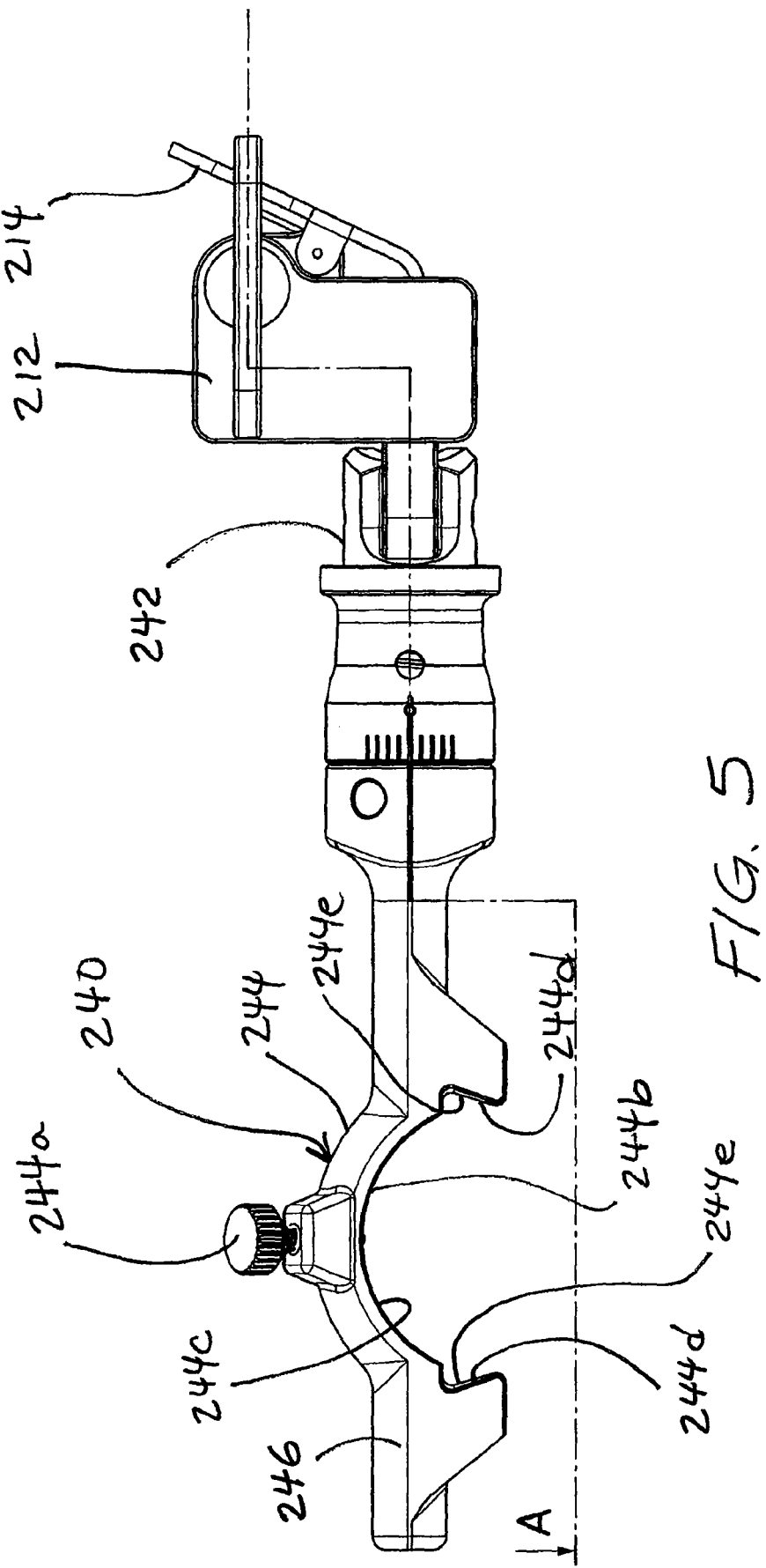
FIG. 5 is a top view of components on the first retractor unit of FIG. 4.

Referring to FIG. 5, slot 244b has sidewalls 244e that taper inwardly like a funnel from the top of the arm to the bottom of the arm. First retractor blade 410 also has tapered sidewalls 418, as shown in FIG. 6, that mate with the tapered sidewalls 244e. The tapered sidewalls of first retractor blade 410 and slot 244b allow the blade to be dropped into the slot from above the arm, while preventing the arm from passing through the slot completely. The tapered sidewalls 244e and 418 are configured to allow insertion of the blade until the top surface of the blade is flush with the top surface of the arm around the slot.

Referring now to FIGS. 5 and 6-8, locking screw 244a extends through first retractor arm 240 and projects into slot 244b. A notch 411 in blade 410 receives the end of locking screw 244a. Locking screw 244a secures blade 410 tightly in slot 244b. Locking screw 244a can be loosened to withdraw the screw from blade 410, allowing the blade to be removed from slot 244b and replaced with another blade. In this arrangement, retractor blades are easily interchangeable in retractor unit 200.

Figure 5A:
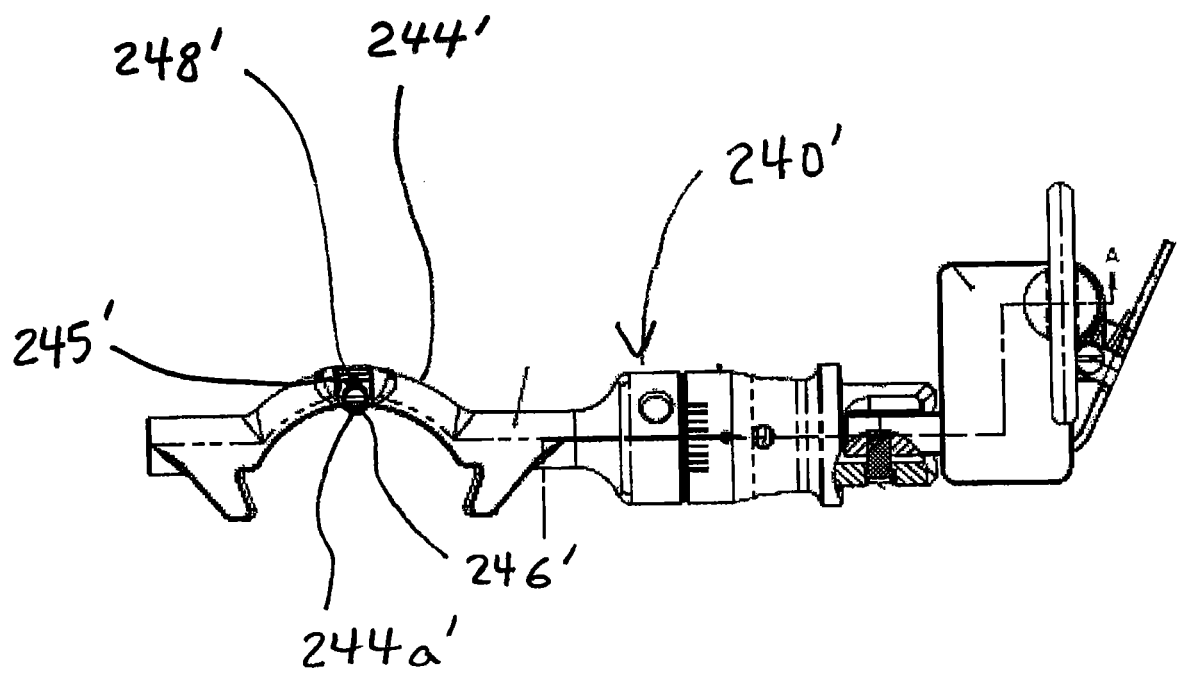
FIG. 5A is a top view of components associated with an alternative retractor unit in accordance with an exemplary embodiment of the invention.

A variety of locking mechanisms may be used to secure the blade in the slot, and the blade support 244 need not have a locking screw. Referring to FIG. 5A, for example, a blade support 244' is shown with a spring loaded pin 244a' extending into the slot. Pin 244a' is partially housed inside a bore 245' in retractor arm 240', and has a rounded end 246' that projects out of the arm into the slot 244b'. A spring 247' is placed behind pin 245' and urges the rounded end 246' outwardly into the slot 244b'. Rounded end 246' is adapted to engage a notch like notch 411 on the rear side of retractor blade 410 to lock the blade in the slot. A pull tab 248' connected to pin 245' extends through the top of the arm. Pull tab 248' can be pulled to retract pin 245' against the spring and withdraw the pin from the slot to release the blade. As a blade is dropped into the slot, rounded end 246' is pushed into the bore until the notch in the blade aligns with the pin. Once the notch aligns with pin 245', the pin snaps out of the bore into the notch to lock the blade to the arm. In this arrangement, a blade can be dropped into the slot 244b' from the top of the retractor (i.e. top-loaded) and locked into the arm in a quick-connect fashion. This top-loading quick-connect mechanism may be utilized on any of the retractor arms described herein.

Figure 9:
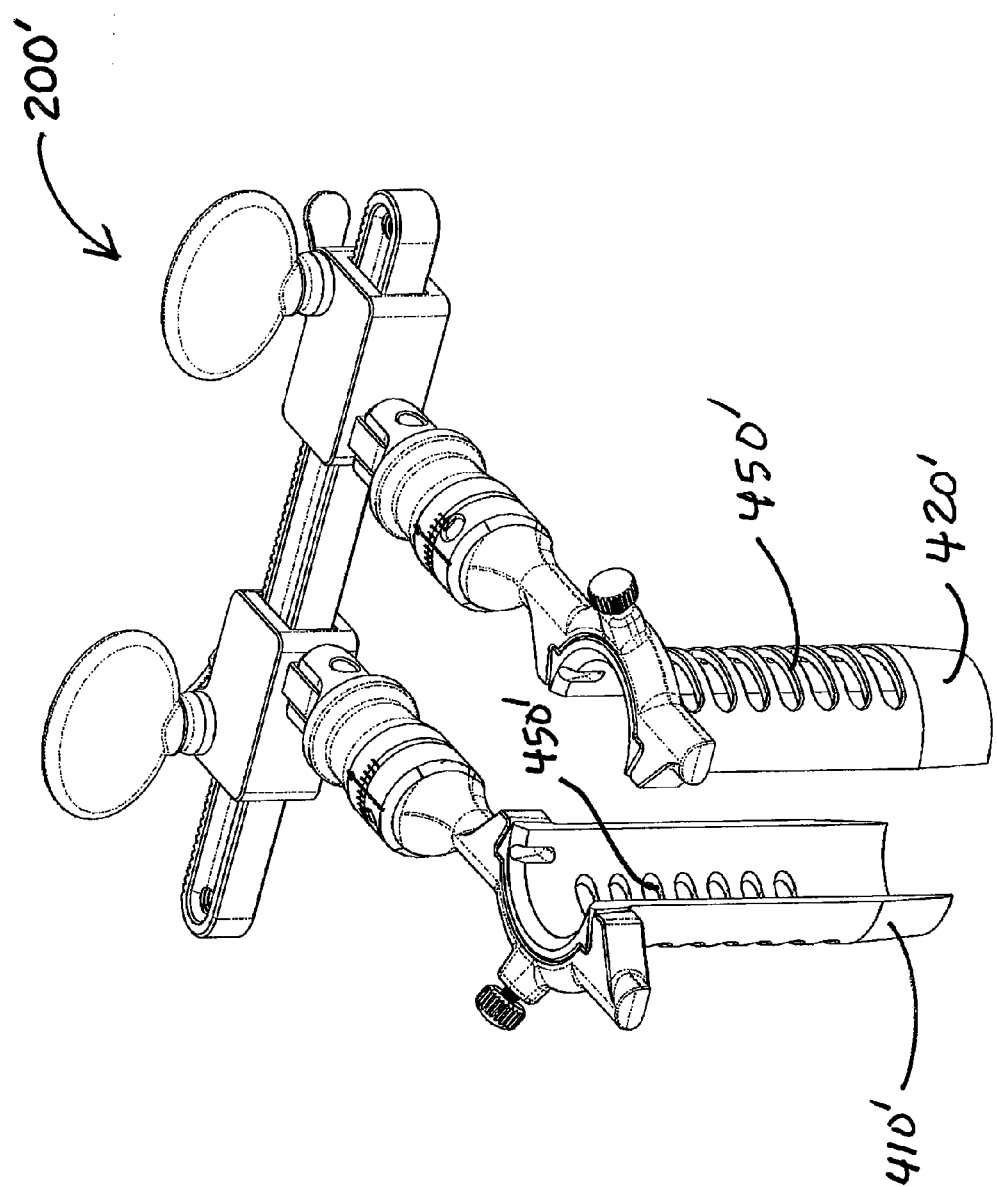
FIG. 9 is a perspective view alternative first retractor unit in accordance with an exemplary embodiment of the invention.
Figure 10:
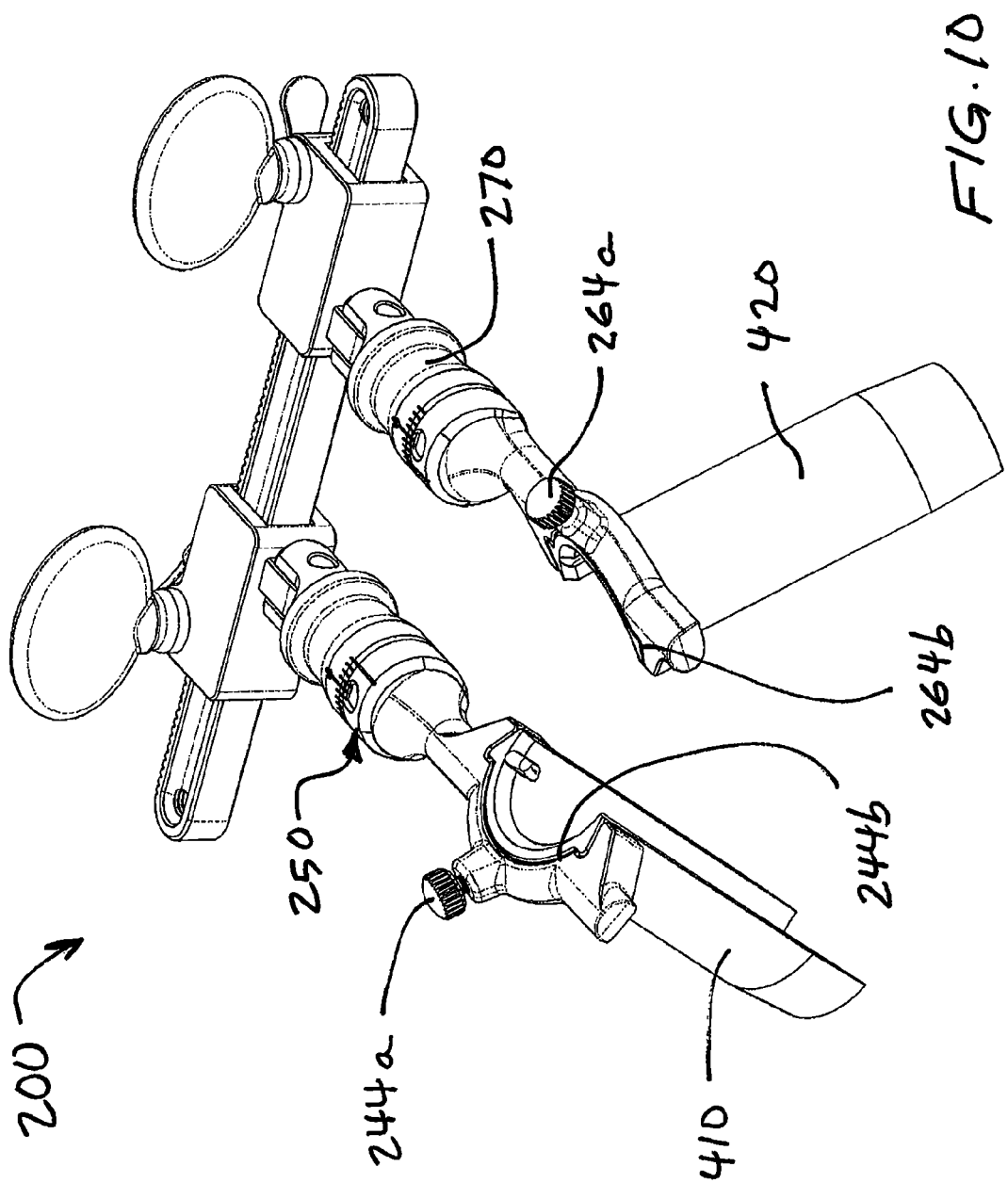
FIG. 10 is a perspective view of the first retractor unit of FIG. 4, shown in a pivoted condition.

Retractor system 100 preferably includes an assortment of different retractor blades that can selected and interchanged. A variety of blade options are preferably provided in a set, each optional blade having unique features, including but not limited to unique lengths, curvatures, fenestrations, points, and edges designed to accommodate or engage bone and tissue. FIG. 9 shows an alternate retractor unit 200' with blades 410' and 420' that have fenestrations 450'.

It is important to maintain retractor blades in a fixed and stable position once the position of their respective support arms are locked in place. Preferred retractors of the present invention provide a much improved blade support by using a special slot and blade geometry. The cross-sectional shapes of the slot and blade conform with one another so that the entire outside face of the blade along the top of the blade is pulled tightly against the inner wall of the slot. This form-fitting blade containment prevents the blade from dangling or rattling loosely from the arm. Such a tight arrangement provides rigidity and stability, unlike loose blade supports which can cause the blade to slip out of an incision, or otherwise shift undesirably.

In FIG. 5, slot 244b has a semi-circular center portion 244c flanked on each side by a keystone shaped edge portion 244d. The keystone shaped edge portions 244d form a trapezoidal shape near the mouth of slot 244b as shown, the trapezoid having a larger width toward the center of the arm and a shorter width at the mouth of the slot. Referring again to FIG. 8, first retractor blade 410 has the same general shape, featuring a semi-circular midportion 412 flanked on each side by a keystone shaped edge portion 413. Midportion 412 aligns precisely with center portion 244c of slot 244b, and edge portions 413 align with edge portions 244d of the slot. The keystone shaped edge portions 244d retain blade 410 in slot 244b and prevent the blade from slipping out of the slot. In this arrangement, blade 410 can only be inserted into slot 244b in a direction normal to retractor arm, and can only slide in the normal direction. The position of the blade 410 is fixed within the slot by locking screw 244a.

Figure 3:
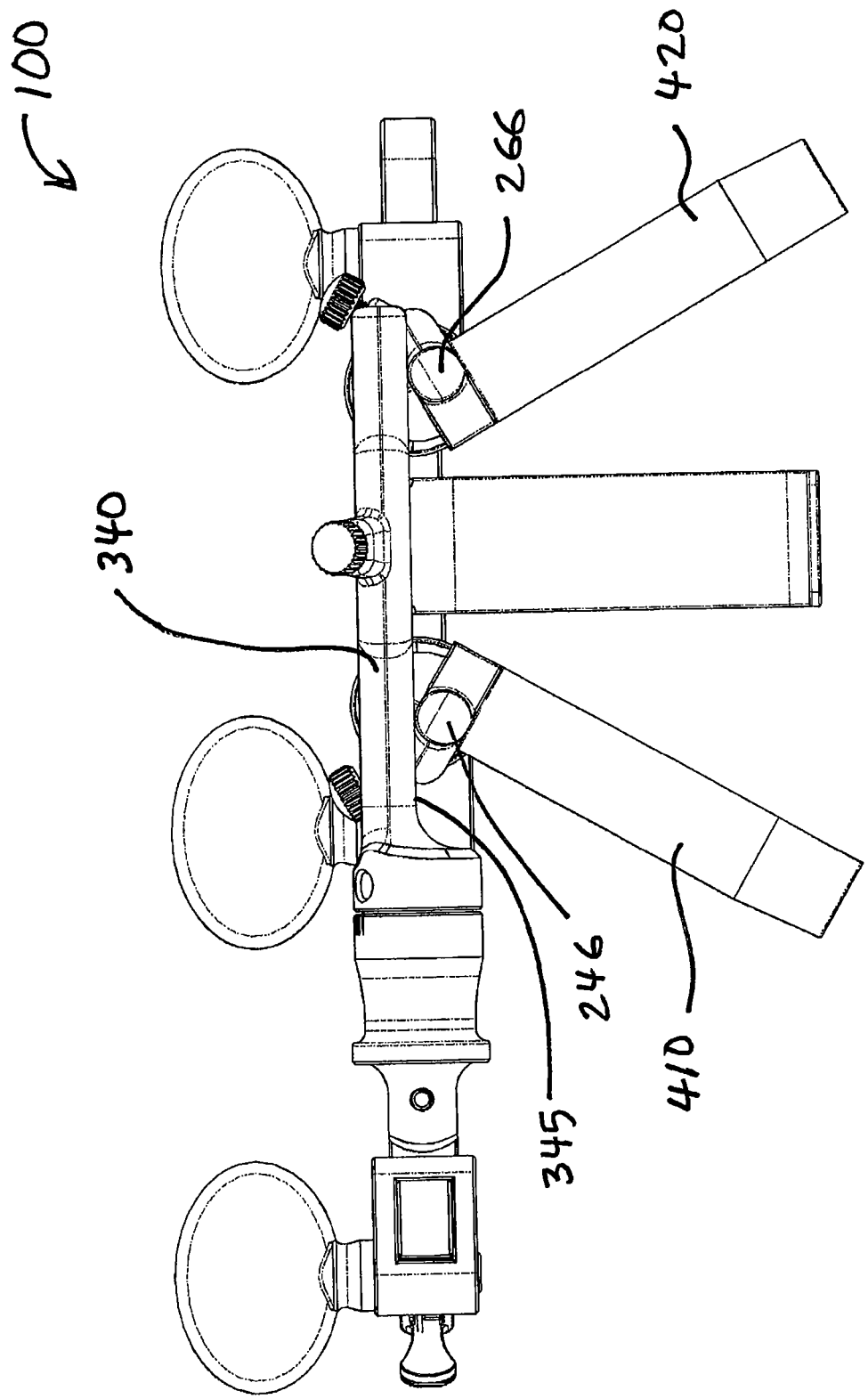
FIG. 3 is a side view of the retractor assembly of FIG. 1.
Figure 11:
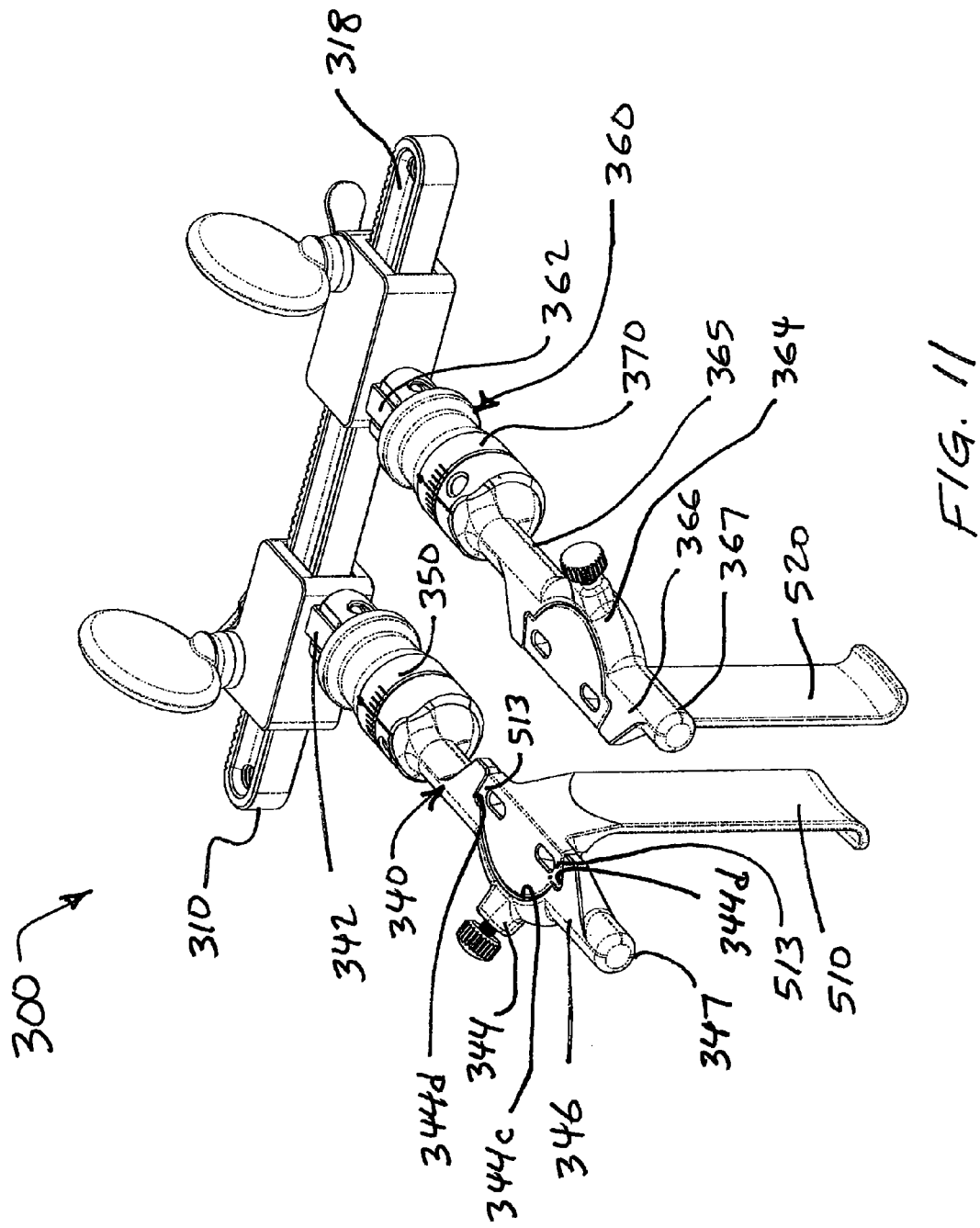
FIG. 11 is a perspective view of a second retractor unit used with the assembly of FIG. 1.

Referring now to FIG. 11, third retractor arm 340 includes a proximal span 342 connected to support mechanism 310 and a distal span 346. A blade support 344 extends between the proximal and distal spans 342 and 346. Proximal span 342 and distal span 346 each include straight portions that are aligned coaxially with one another. Straight portions each have a recessed underside 345, seen more clearly in FIG. 3. In this configuration, third retractor arm 340 has a reduced thickness along the straight portions. Blade support 344 also has a recessed underside. The undersides of the straight portions and underside of blade support 344 form a continuous gliding surface 341 that extends between the proximal span 342 and distal span 346. Gliding surface 341 has a rounded convex contour that smoothly engages guide track 241 on first retractor arm 240. The underside of third retractor arm 340 slides over distal spans 246 and 266 of first and second retractor arms 240 and 260, respectively.

Proximal span 342 is connected to third lateral adjustment assembly 312 by a pin connection and hinge. The hinge allows third retractor arm 340 to pivot in a plane generally perpendicular to rack 318. The pivot arrangement allows retractor arm 340 to be raised or lowered with respect to the incision so that the vertical orientation of the blade is properly aligned or square with the incision. The hinge also allows for minor adjustment of the arm's position to maintain a flat nested arrangement with the other retractor arms.

Blade support 344 connects third retractor arm 340 to third retractor blade 510. Third retractor blade 510 is secured to blade support 344 by a locking screw 344a that extends through a screw hole in the retractor arm. A slot 344b receives third retractor blade 510 and has a geometry that conforms to the cross-sectional shape of the third retractor blade. Locking screw 344a extends through third retractor arm 340 and projects into slot 344b. A notch in blade 510 receives the end of locking screw 344a, like notch 411 in blade 410. Locking screw 344a secures blade 510 tightly in slot 344b. Locking screw 344a can be loosened to withdraw the screw from blade 510, allowing the blade to be removed from slot 344b and replaced with another blade. In this arrangement, retractor blade 510 is easily interchangeable in the retractor unit 300. As noted above, retractor system 100 preferably includes an assortment of different retractor blades that can be selected and interchanged with one another.

Referring to FIGS. 2 and 11, slot 344b has a rounded midportion portion 344c flanked on each side by a keystone shaped edge portion 344d. The keystone shaped edge portions 344d give the slot a generally trapezoidal shape. The trapezoidal shape has a larger width toward the center of the arm and a shorter width at the mouth of the slot. Third retractor blade 510 has the same general shape, featuring a curved midportion 511 flanked on each side by a keystone shaped edge portion 513. Midportion 511 aligns precisely with midportion 344c of slot 344b, and edge portions 513 align with edge portions 344d of the slot. The keystone shaped edge portions 344d, in combination with tapered sidewalls similar to those discussed in arm 240, retain blade 510 in slot 344b and prevent the blade from slipping out of the slot. In this arrangement, blade 510 can only be inserted into slot 344b in a direction normal to retractor arm 340, and can only slide in the normal direction. The position of the blade 510 is fixed within the slot by a locking screw 344a. As noted above, a quick-connect lock can also be used.

An important feature of retractor 100 is the full support provided for the retractor unit 300. Retractor arms 340 and 360 on retractor unit 300 are each supported underneath at two locations. In particular, retractor arm 340 is supported by the distal spans 246 and 266 of retractor unit 200. Retractor arm 360 is supported by the proximal spans 242 and 262 of retractor unit 200. This keeps both of the upper arms 340 and 360 supported and parallel with one another, providing stability and control over the relative positions of blades 510 and 520.

Retractor arms 240, 260, 340 and 360 are each independently displaceable on their respective support assembly or mechanism. Unlike assemblies that allow only one side of the retractor to move, retractor units 200 and 300 permit the surgeon to move any of the arms. To widen the incision width between blades 410 and 420, for example, retractor arm 240 can be moved away from arm 260 while keeping arm 260 fixed, or arm 260 can be moved away from arm 240 while keeping arm 240 fixed. Alternatively, both arms 240 and 260 can be moved away from one another. This flexibility provides greater control over how the incision is expanded.

Retractor arms 240, 260, 340 and 360 each include a non-rotating portion and a rotating portion. The rotating portion allows the blade support and blade to be pivoted with respect to the axis of the arm. Referring to FIG. 4, for example, retractor unit 200 is shown with blades 410 and 420 in a generally parallel arrangement. In FIG. 1, blades 410 and 420 are pivoted away from one another. The blade positions in FIG. 1 illustrate a fairly large pivot angle that could be used to spread apart tissue deep inside an incision. The blades are pivotable in very small increments, however, allowing for very small angles of adjustment. In a preferred embodiment, the blades may be pivoted and locked at increments of about 5 to about 10 degrees.

Figure 12:
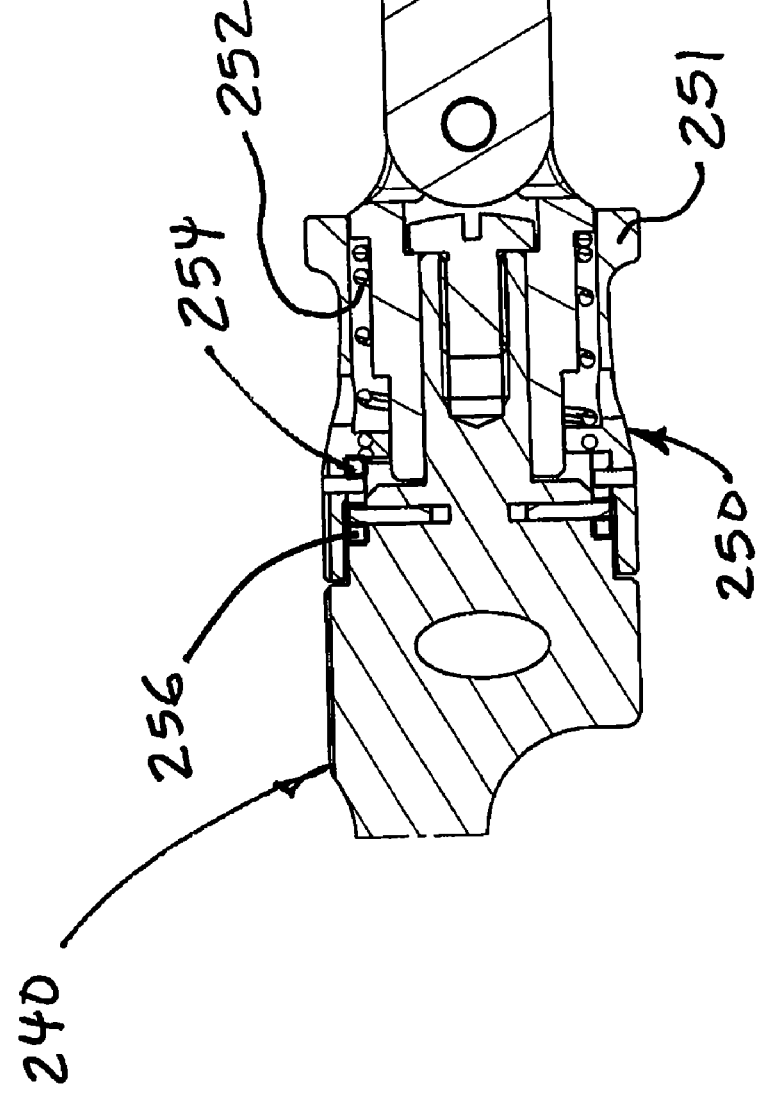
FIG. 12 is a side view of components on the first retractor unit of FIG. 4 shown in partial cross-section.

Each of retractor arms 240, 260, 340 and 360 includes a self-locking in-line pivot mechanism 250, 270, 350 and 370, respectively. Pivot mechanisms 250, 270, 350 and 370 are identical to one another. Therefore, pivot mechanism 250 will be described with the understanding that pivot mechanisms 270, 350 and 370 have the same components and operation. Referring to FIG. 12, pivot mechanism 250 includes a cylindrical knob 251 having a longitudinal axis that is generally aligned with the axis of retractor arm 240. Knob 251 houses a pair of locking rings 254 and 256. Locking rings 254 and 256 have toothed surfaces 254a and 256a that engage with one another to lock the orientation of the arm. Locking ring 254 is fixed relative to knob 251, while locking ring 256 is fixed to the rotating portion of arm 240.

A compression spring 252 is housed inside the knob and circumscribes the non-rotating portion of retractor arm 240. Spring 252 urges knob 251 toward the distal span, to push locking ring 254 into engagement with locking ring 256. In this arrangement, knob 251 is axially displaceable between a locking position and an unlocking position. In the locking position, knob 251 is pushed by the spring until the teeth 254a of locking ring 254 engage teeth 256a of locking ring 256. Because locking ring 256 is engaged with the fixed locking ring 254, the rotating portion of arm 240 cannot be pivoted, preventing blade support 244 and blade 410 from being pivoted. In the unlocking position, knob 251 is pulled back against the bias of spring 252 so that locking rings 254 and 256 are separated. In this condition, fixed locking ring 254 no longer holds locking ring 256, permitting the blade support 244 and blade 410 to be pivoted.

The teeth 254a and 256a allow the orientation of blade 410 to be adjusted and locked at increments of about 7.5 degrees. This allows the surgeon to finely adjust the pivot angle of each blade and lock the retractor arm at that angle. Larger teeth may be used to provide larger increments of adjustment, and smaller teeth may be used to provide smaller increments of adjustment. The retractor arms may be pivoted by twisting the rotating portion of the arm when the knob is moved to the unlocking position. Alternatively, the arm may be pivoted by inserting a turning rod or other implement into the arm. Referring to FIG. 4, retractor arm 240 includes a small hole 243 at the top of the arm. A turning rod may be inserted into hole 243 to rotate the arm.

When blades are tilted in an incision, the tissue may exert some resistance that pulls the retractor arm downwardly toward the incision. The nested arrangement of the retractor arms keeps the upper retractor arms supported and parallel to one another.

Figure 13:
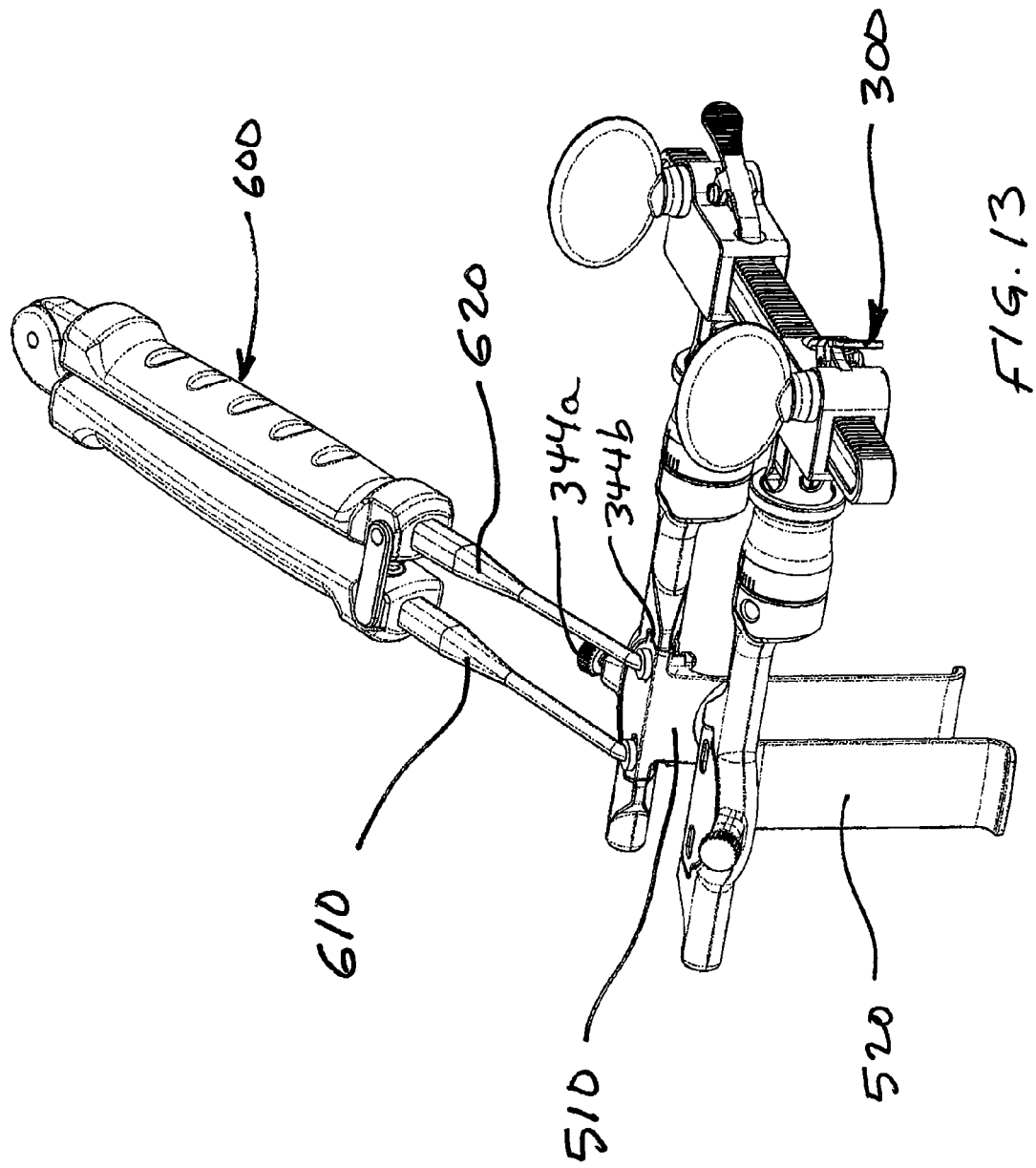
FIG. 13 is a perspective view of the second retractor unit of FIG. 11, with a blade insertion tool in accordance with one exemplary embodiment of the invention.

Referring to FIG. 2, the retractor arms form a generally rectangular opening that provides an adjustable field of view. A retractor blade may be removed and replaced by top-loading another replacement blade into the slot. Top-loading the replacement blade may be performed after the retractor has been inserted into the incision. Because the rectangular opening is relatively small, and because the retractor arms can be inadvertently bumped, removal and insertion of retractor blades is preferably done with narrow instruments that can be maneuvered easily between the arms. In preferred embodiments, the retractor assembly 100 includes instrumentation designed to insert and remove retractor blades with minimal disturbance to the retractor assembly. Referring to FIG. 13, a blade handle 600 is shown connected with blade 510 of retractor unit 300. Blade 510 includes two small slots 515 that extend through a top portion of the blade. Blade handle 600 includes a pair of clamp arms 610 and 620 that are received into slots 515. Clamp arms 610 and 620 are interconnected and can be squeezed or compressed to move clamp arms 610 and 620 close together. In this arrangement, when clamp arms 610 and 620 are inserted into slots and the mechanism is operated, the arms clamp the top portion of blade 510. After loosening locking screw 344a on blade support 344, blade 510 can be lifted out of slot 344b with blade handle 600. A replacement blade may be gripped with the clamp arms of blade handle 600 in the same manner, and inserted into slot 344b of third retractor arm 340.

As noted above, retractor unit 200 can be used either alone as a cylindrical access tube, or nested with another retractor unit, such as retractor unit 300. That is, a surgeon can opt to use retractor unit 200 alone as a cylindrical access port when the procedure does not require a significant expansion of the incision. The surgeon can opt to spread apart retractor arms 240 and 260 of retractor unit 200, and nest another retractor unit on top of retractor unit 200 if the incision needs to be expanded in two directions. The ability to add a second retractor unit onto retractor unit 200 gives the surgeon a choice that can be deferred until after retractor unit 200 is inserted into the incision.

Figure 14:
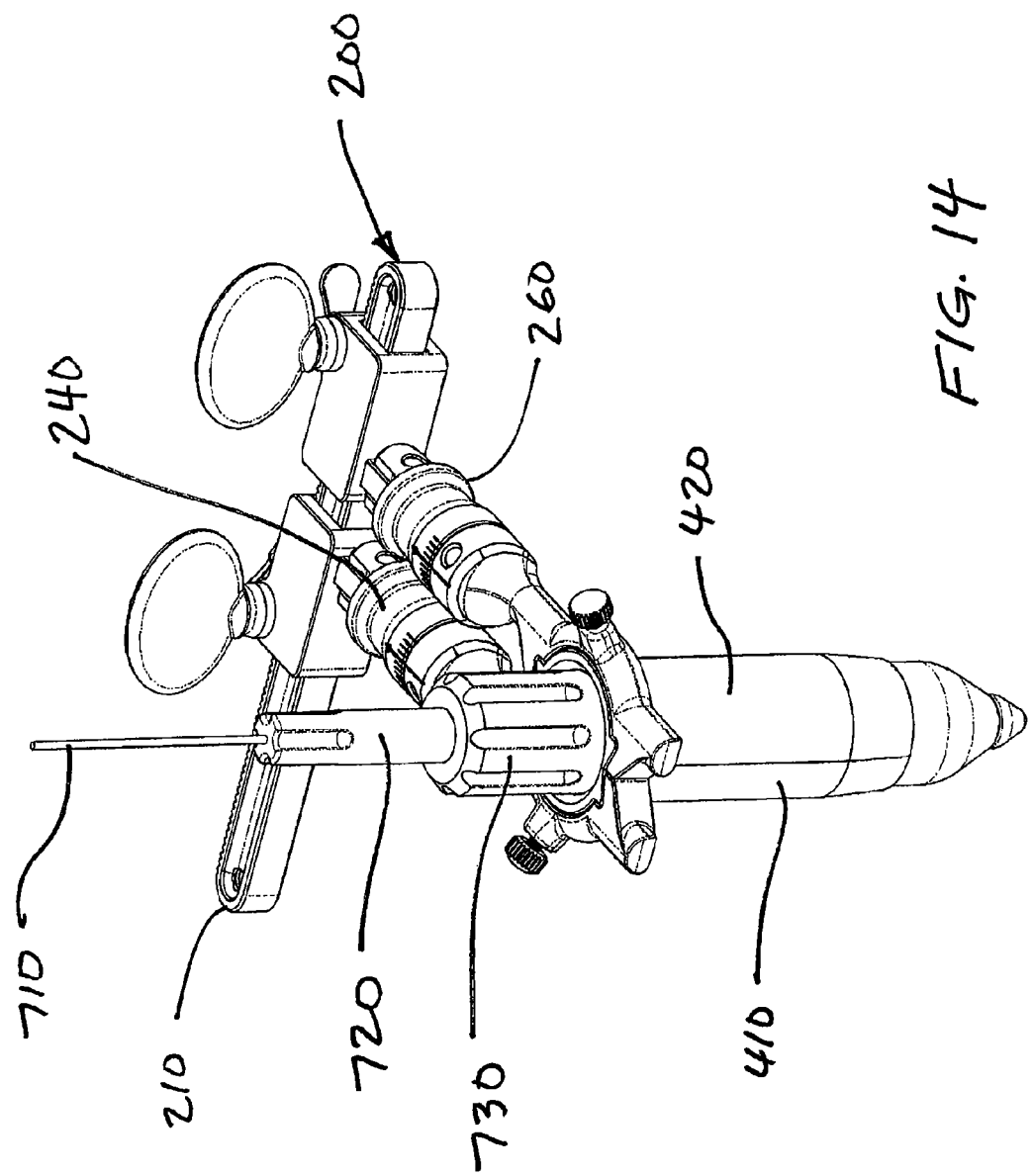
FIG. 14 is a perspective view of the first retractor unit of FIG. 4 shown with components for dilating an incision.

Retractor unit 200 is inserted into an incision using a guide wire and one or more dilators. Referring to FIG. 14, retractor unit 200 is shown after being placed over a guide wire 710, a first dilator 720 and a second dilator 730. Retractor arms 240 and 260 are brought together in a closed position, so that retractor blades 410 and 420 abut one another to form a cylindrical tube. The cylindrical tube is generally coaxial with the guide wire and dilators. Once the blades 410 and 420 are inserted into the incision, and the support assembly is properly fixed with respect to the operating field, the guide wire and dilators can be removed out of the access tube.

Figure 15:
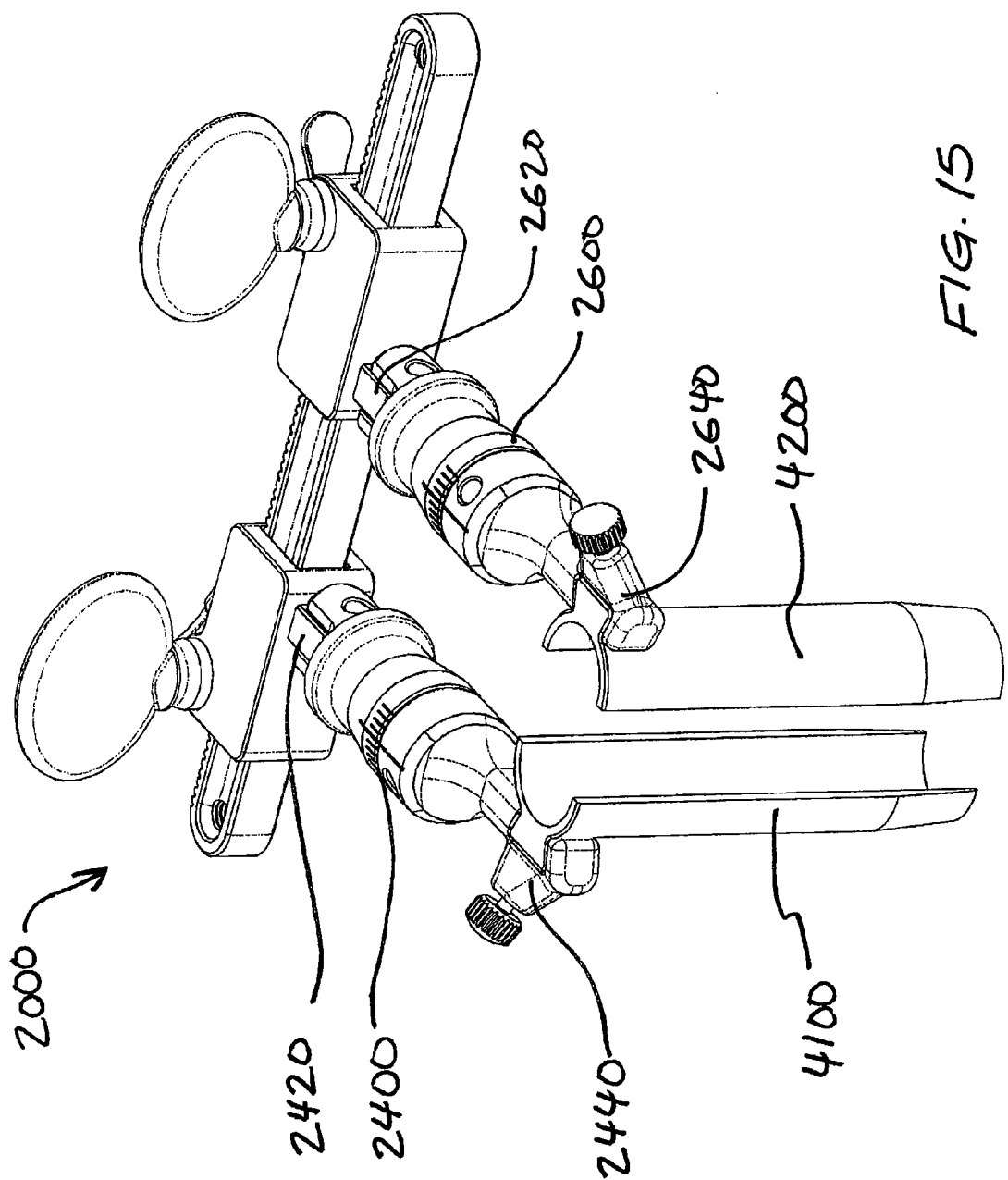
FIG. 15 is a perspective view of a third retractor unit in accordance with an exemplary embodiment of the invention.
Figure 16:
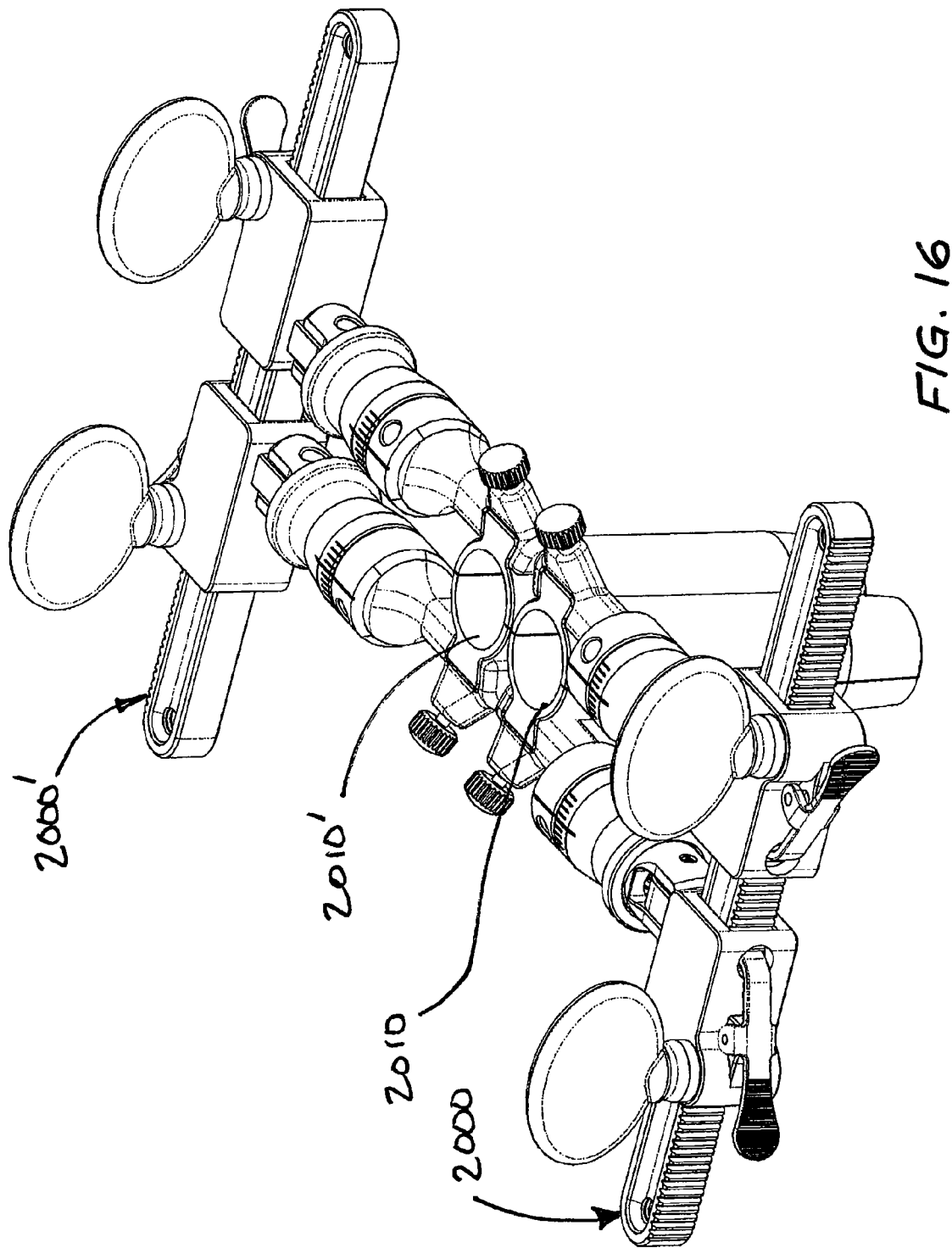
FIG. 16 is a perspective view of the third retractor unit of FIG. 15 arranged in a mirror arrangement with a fourth retractor unit in accordance with an exemplary embodiment of the invention.

Referring now to FIG. 15 an alternative retractor unit or "percutaneous retractor" 2000 is shown in accordance with another exemplary embodiment of the invention. Retractor unit 2000 is intended for providing access for a single screw only, with the option of spreading open the access port, as will be described. Retractor unit 2000 is similar in many respects to retractor unit 200, but is designed to work in an end to end configuration with another retractor unit, through which a neighboring screw is inserted. An end to end configuration is shown, for example, in FIG. 16 which shows this percutaneous-type retractor unit 2000 arranged end to end with retractor unit 2000'. As will be described, this arrangement allows an elongated rod to be inserted through a first incision, turned or steered subcutaneously toward a second incision, and advanced to the second incision to implant the rod between the incisions.

Retractor units 2000 and 2000' are identical, and have many features in common with retractor unit 200. For purposes of description, only retractor unit 2000 will be described. Retractor unit 2000 includes a pair of parallel retractor arms 2400 and 2600 that support retractor blades 4100 and 4200, respectively. Retractor blades each have a semi-circular cross-sectional shape, and form a cylindrical access portal 2010 when the blades are brought together. Portal 2010 has a relatively small diameter, which may be as small as about 16 mm or smaller, to facilitate a more minimally-invasive or "percutaneous" access to an area beneath the incision. Retractor arms 2400 and 2600 respectively include proximal spans 2420 and 2620, and blade supports 2440 and 2640. Unlike the arms on retractor unit 200, retractor arms 2400 and 2600 do not have distal spans. Instead, the distal ends of retractor arms 2400 and 2600 terminate at blade supports 2420 and 2620. In this arrangement, blade supports 2420 and 2620 can be arranged end to end with retractor unit 2000', or another retractor assembly, so as to place portal 2010 in close proximity to another access portal. This arrangement is desirable where two bone screws are spaced close together and require access using minimally invasive techniques.

Like retractor unit 200, retractor units 2000 and 2000' give the surgeon the option of initially accessing the operating field through a relatively small incision through a closed access port, and subsequently expanding the incision if needed. This gives the surgeon the ability to begin a procedure through the closed access port, thereby minimizing disturbance to tissues, and subsequently decide whether the incision must be expanded by moving the arms, by tilting the blades, or both. If the procedure can be completed without opening retractor blades 4100 and 4200, then further disturbance of tissues can be minimized. If the incision must be expanded, the surgeon can move apart the retractor blades and/or pivot them to spread apart tissue as needed. This flexibility of operation provides the final part of the developmental aid that surgeons in training can use. Surgeons may initially elect to expand the retractor blades before beginning a procedure. As they gain more experience, the surgeons have the option of keeping the retractor blades closed. Using this adaptive learning procedure, surgeons can gradually work toward using smaller and smaller incisions during their procedures.

Surgeons may also work toward using smaller and smaller incisions by progressing from the minimally-invasive retractor units 200 and 300, having openings of about 24 mm in diameter, for example, to the much smaller percutaneous retractor units 2000 and 2000', having openings of about 16 mm in diameter, for example. A surgeon may begin by using the nested retractor units 200 and 300 and take advantage of the ability to expand the incision along both the cranial-caudal axis and medial-lateral axis. The surgeon may then progress to using only the lower retractor unit 200. With additional practice and experience, the surgeon may progress further to using a single percutaneous retractor 2000, instead of the lower retractor unit 200.

Referring now to FIG. 17, retractor 2000 is shown in an end to end configuration with retractor 2000'. Retractor arms 2400 and 2600 are spread apart to increase the working area through retractor blades 4100 and 4200. In addition, the arms 2400 and 2600 are spread apart to separate the blades and form a gap through which a spinal rod can be tilted or turned, and then maneuvered subcutaneously toward an adjacent incision held open by retractor 2000'.

Retractor arms 2400' and 2600' on retractor 2000' remain closed. By opening blades 4100 and 4200, gaps are formed between the two blades, which provides turning or tilting room for instruments that are used between the blades. Instrument "I" is schematically shown in a tilted configuration between blades 4100 and 4200. The ability to split apart blades 4100 and 4200 allows an elongated implant, such as a spinal fixation rod, to be advanced down between blades 4100 and 4200 and turned subcutaneously toward a second location. For example, a spinal fixation rod could be inserted down between blades 4100 and 4200, turned approximately ninety degrees beneath the incision, and advanced toward a rod receiving anchor underneath retractor 2000'. In this sense, blades 4100 and 4200 are dividable to create a gap "G" for the rod. Gap G may be created by laterally adjusting the positions of the retractor arms. In addition, or as an alternative, the gap may be created by tilting the bottoms of the blades away from another. Using the tilting method has the advantage of creating the gap beneath the incision where it is needed, while keeping the top of the blades closer together, and thereby minimizing the disturbance of tissue at or near the skin surface.

Figure 18A:
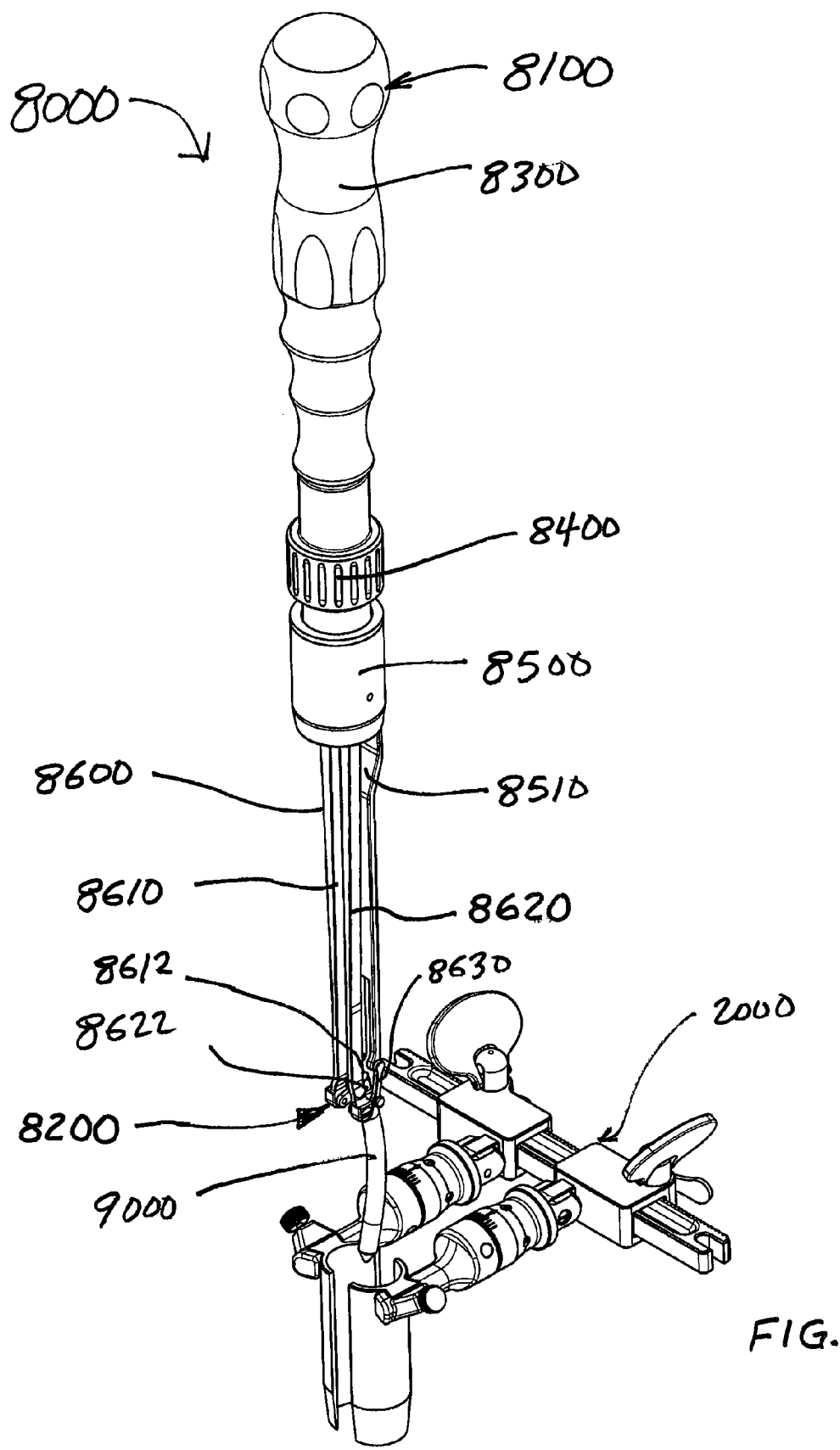
FIG. 18A is a perspective view of the retractor unit of FIG. 15 with a rod and rod insertion instrument in a first mode of operation.
Figure 18B:
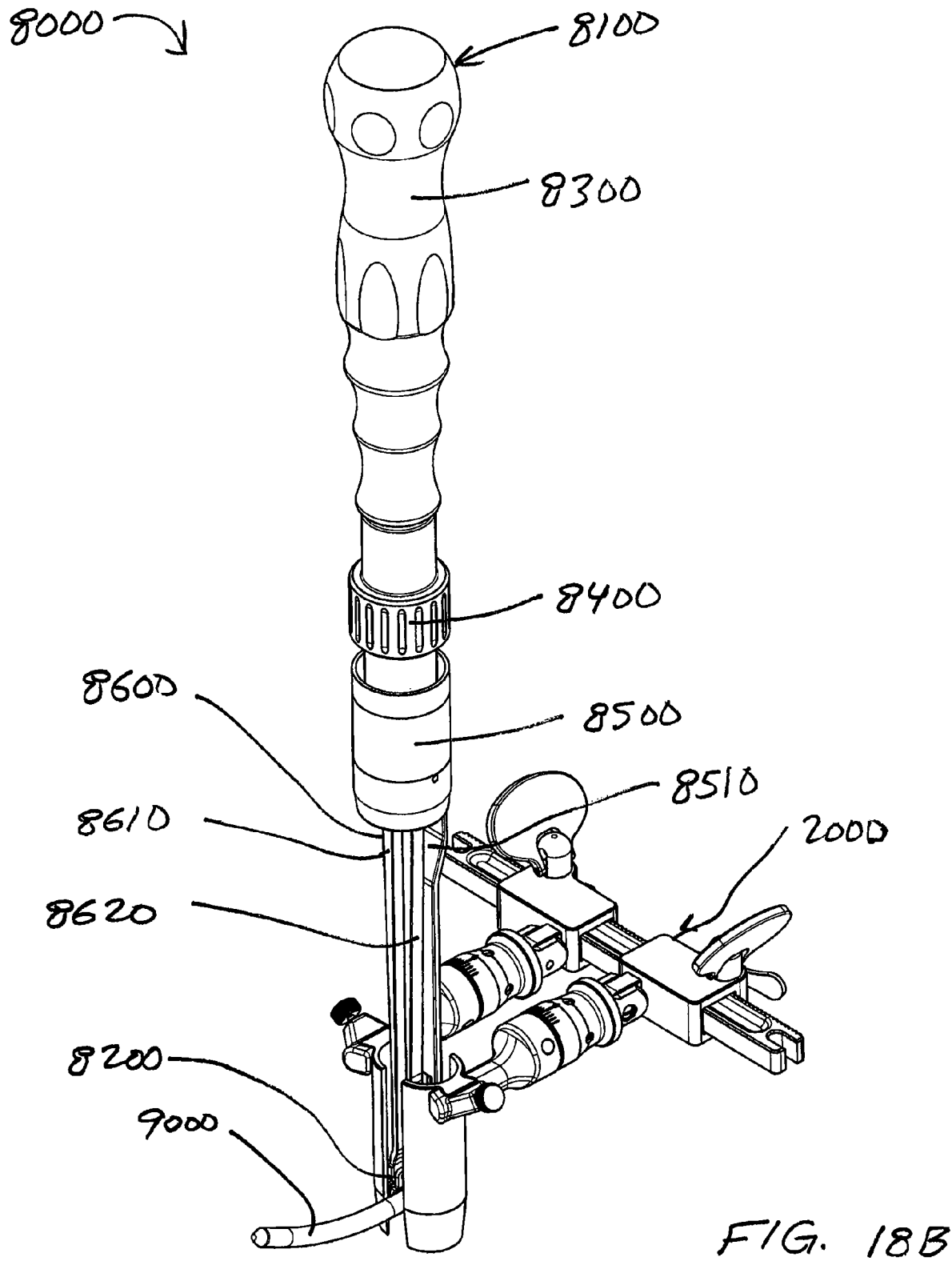
FIG. 18B is a perspective view of the retractor unit of FIG. 15 with a rod and rod insertion instrument in a second mode of operation.

Referring now to FIGS. 18A and 18B, a rod insertion instrument or "rod inserter" 8000 is shown in accordance with an exemplary embodiment of the invention. Rod inserter 8000 is operable to advance a spinal fixation rod through an access port, such as portal 2010 formed by retractor unit 2000. In addition, rod inserter 8000 is operable to change the orientation of the rod by turning or "steering" the rod after the rod is beneath the tissue at the desired depth. Once the rod is turned, rod inserter 8000 is operable to advance the rod subcutaneously to a second location beneath the tissue. By this procedure, the elongated rod is inserted beneath the tissue and advanced percutaneously to the nearby location. This is in contrast to prior methods which expose locations by making large incisions and displacing large sections of tissue. By steering and advancing the rod beneath tissue, the surgeon can reduce the size of incisions and the amount of tissue damage.

Rod inserter 8000 includes a proximal end 8100 that is operated by the user, and a distal end 8200 which manipulates a rod 9000. Proximal end 8100 includes a handle 8300 for supporting the instrument in one hand, and clamping knob 8400 positioned adjacent the handle. A pair of clamping arms 8610 and 8620 extend from clamping knob 8400. Clamping arms 8610 and 8620 each have a rod clamp 8612 and 8622, respectively, for engaging a rod. Rod clamps 8612 and 8622 are movable between a clamping position, in which the clamps are moved toward one another to clamp around a rod, and a release position, in which the clamps are spread apart. Clamping knob 8400 has an internal threading that engages external threading on handle 8300. Rotation of knob 8400 causes the knob to move axially with respect to clamping arms. The interior of clamping knob 8400 compresses clamping arms 8610 and 8620 together as the knob is moved toward the rod clamps 8612 and 8622. In this arrangement, clamping knob 8400 can be turned and moved down the clamping arms to squeeze the rod clamps together.

Rod clamps 8612 and 8622 are pivotally mounted to the instrument and connect with linkages 8630 that allow the clamps the pivot the orientation of rod 9000 when the rod is held between the clamps. A sliding collar 8500 is operatively coupled with linkages 8630 to control the pivot motion of rod 9000. Collar 8500 has a long stem portion 8510 that extends parallel to clamp arms 8610 and 8620 and connects with linkages 8630. As collar 8500 is advanced toward or away from rod 9000, stem 8510 pivots linkages 8630 and the rod. Pulling collar 8500 away from rod 9000 pivots the rod toward an axial orientation that is parallel to clamp arms 8610 and 8620. Pushing collar 8500 toward clamps 8612 and 8622 pivots the rod to an orientation generally perpendicular to the clamp arms. With this instrument, rod 9000 can be brought to an orientation substantially parallel to clamp arms 8610 and 8620, as shown in FIG. 18A, and inserted down an access portal, such as portal 2010, to a position beneath an incision. In doing so, rod 9000 is advanced down the portal in an orientation generally parallel to the access of the portal. Instrument 8000 can further be operated to turn the orientation of the rod so the rod is generally normal to the axis of the portal, as shown for example in FIG. 18B. Once rod 9000 is turned, instrument 8000 can advance a leading end of the rod subcutaneously to a second location beneath tissue. The leading end of the rod can be advanced until it is received by a rod fixation screw or other component for securing the rod.

Figure 24:
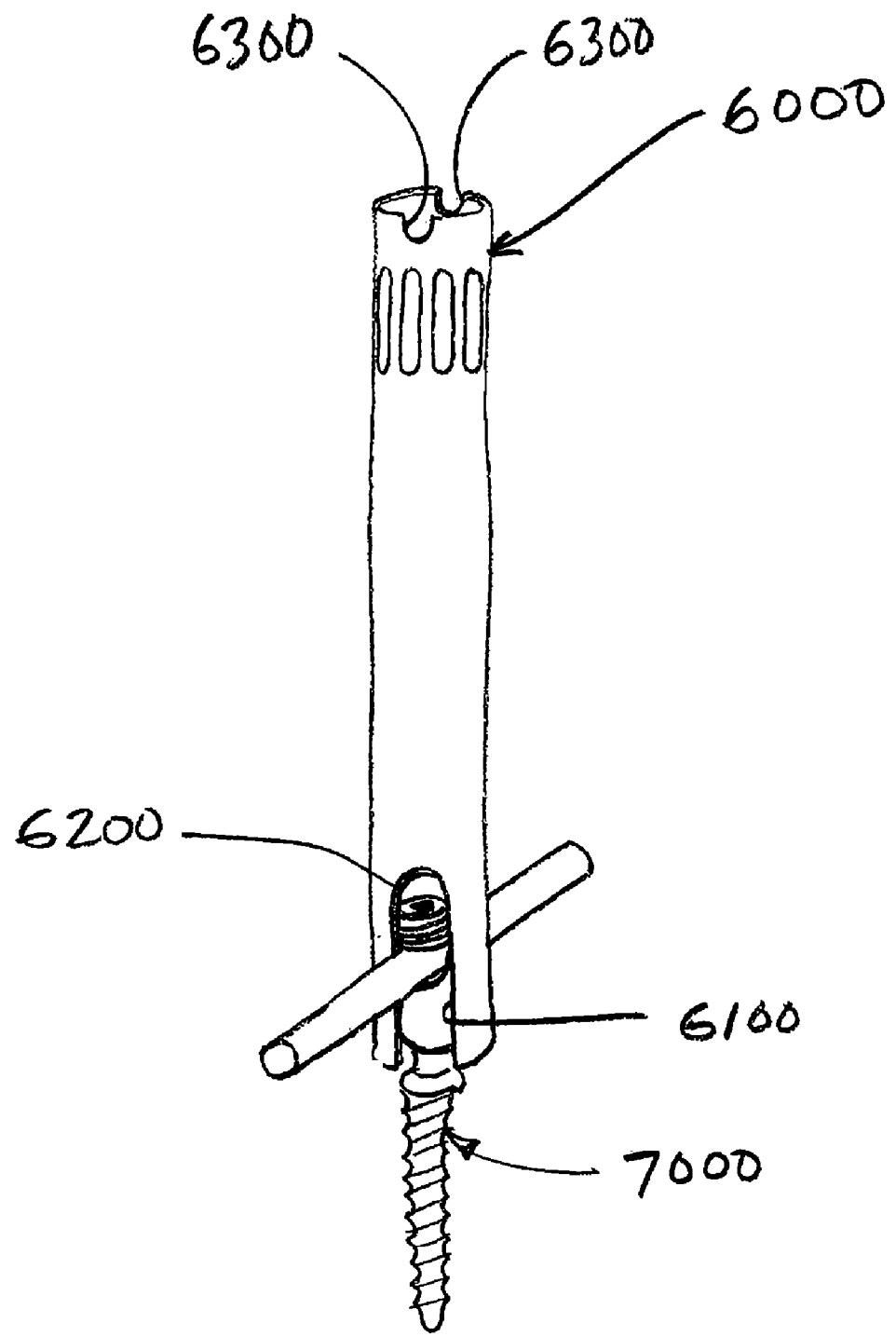
FIG. 24 is a perspective view of an extension tube, spinal fixation rod, and rod anchor in accordance with an exemplary embodiment of the invention.
Figure 25:
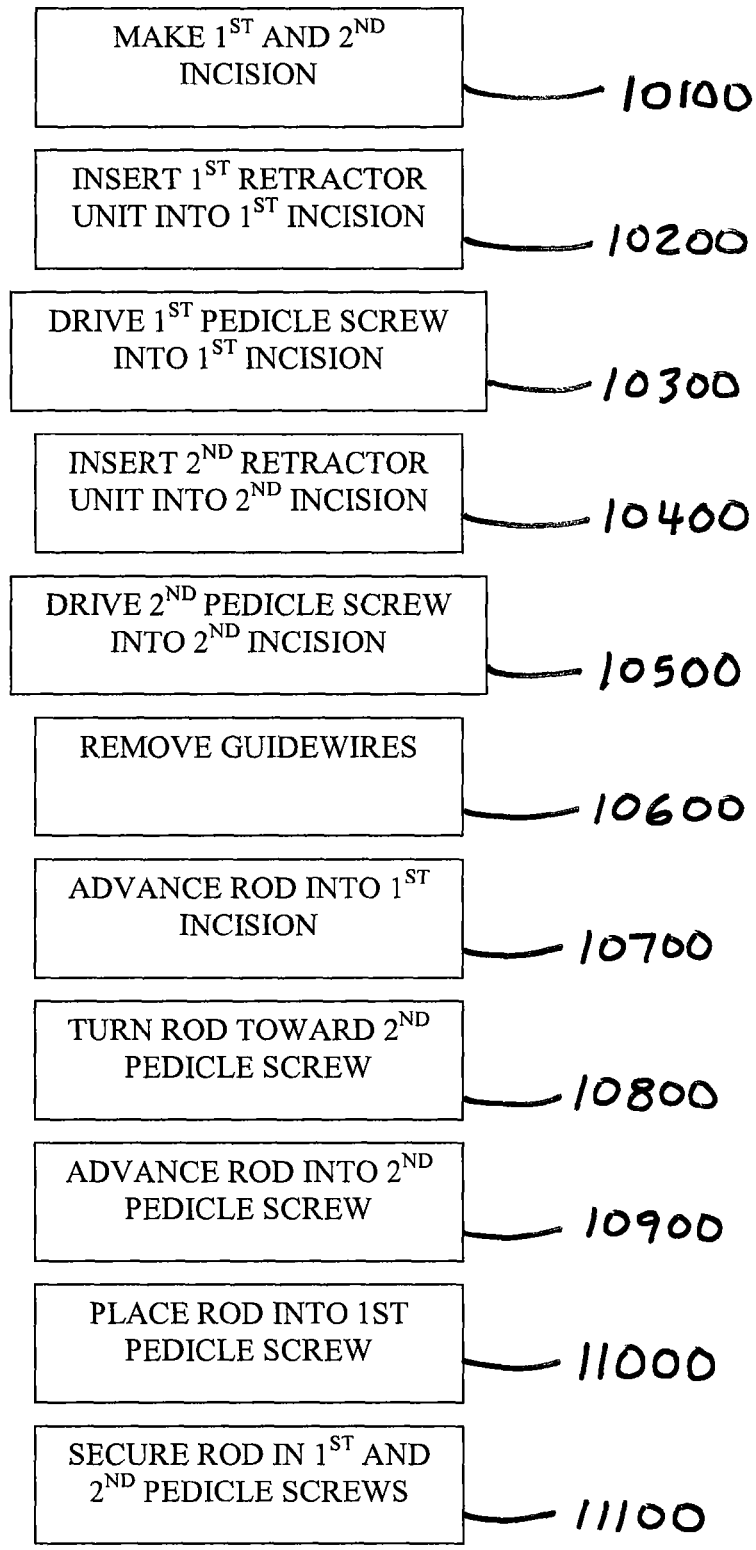
FIG. 25 is a perspective of another extension tube, rod anchor and orientation tool in accordance with an exemplary embodiment of the invention.

In the procedure outlined above, the rod is inserted and turned through one incision. Such a procedure may be carried out using only one percutaneous retractor unit. The adjacent incision may not need a percutaneous retractor, and can be held open with a non-dividable extension tube. One example of a non-dividable extension tube is shown by extension tube 6000 in FIG. 24. Extension tube 6000 includes a pair of inverted U-shaped slots 6100 at the bottom of the tube that allows a rod to be inserted into a rod receiving anchor, such as the polyaxial screw assembly 7000 shown beneath the tube. A number of polyaxial screw assemblies may be used in conjunction with the invention, including but not limited to, for example, the polyaxial screw components shown in U.S. Pub. No. 2006/0217735, the contents of which are incorporated by reference in their entirety. Each slot 6100 includes a flared or funnel shaped edge 6200 that becomes wider at the outer circumference of the tube 6000. Funnel shaped edge 6200 provides a smooth contour around the slot that makes it easier to insert the rod into the tube. Extension tube 6000 also includes a pair of notches 6300 at the top of the tube that are aligned with slots 6200. Notches 6300 provide a visual aid that helps the surgeon determine the orientation of the slots 6200 when the bottom of the tube is inserted into the incision.

Prior to advancing the rod through muscle tissue to the adjacent rod anchor, the rod anchors beneath the incisions must be in proper alignment to receive the rod. In a preferred embodiment of the invention, the components cooperate with an orientation tool or "orientator" that is operable to engage the rod receiving head of the rod anchors and rotate them so their rod receiving channels are aligned to receive a rod. Referring now to FIG. 26, an extension tube 6000' similar to extension tube 6000 is shown with an orientator 6700 and a rod anchor 7000. Orientator 6700 can be inserted through extension tube 6000' into engagement with the rod anchor and rotated to adjust the orientation of the rod anchor. Extension tube 6000' includes a pair of diametrically opposed flexible tabs 6100' (one of which is visible) in FIG. 26) that snap into engagement with a pair of diametrically opposed grooves 6750 on orientator 6700. In this arrangement, tabs 6100' snugly hold orientator 6700 in a snug engagement.

In FIG. 27, orientator 6700 includes a proximal end 6710 with a handle 6715 and a distal end 6720 with an alignment bar 6730. Alignment bar 6730 is configured for insertion into the rod receiving channel of rod anchor 7000. A pair of resiliently flexible wall sections 6740 extend above alignment bar 6730 and are configured to be compressed inwardly slightly as they contact the sides of the U-shaped channels in rod anchor 7000. The engagement between wall sections 6740 and the U-shaped channels is sensed tactilely by the surgeon, signaling that alignment bar is properly in place. The radial positions of grooves 6750 correspond or align with the U-shaped channels in rod anchor 7000, and indicate the direction of alignment bar 6730. When tabs 6100' are engaged in grooves 6750, alignment bar 6730 is set in the proper orientation to pass into the U-shaped channel of the rod anchor. Once bar 6730 is inserted into the rod receiving anchor, handle 6715 can be rotated to rotate the rod receiving body of the rod anchor so that the U-shaped channels are parallel to the desired rod orientation.

Figure 19:
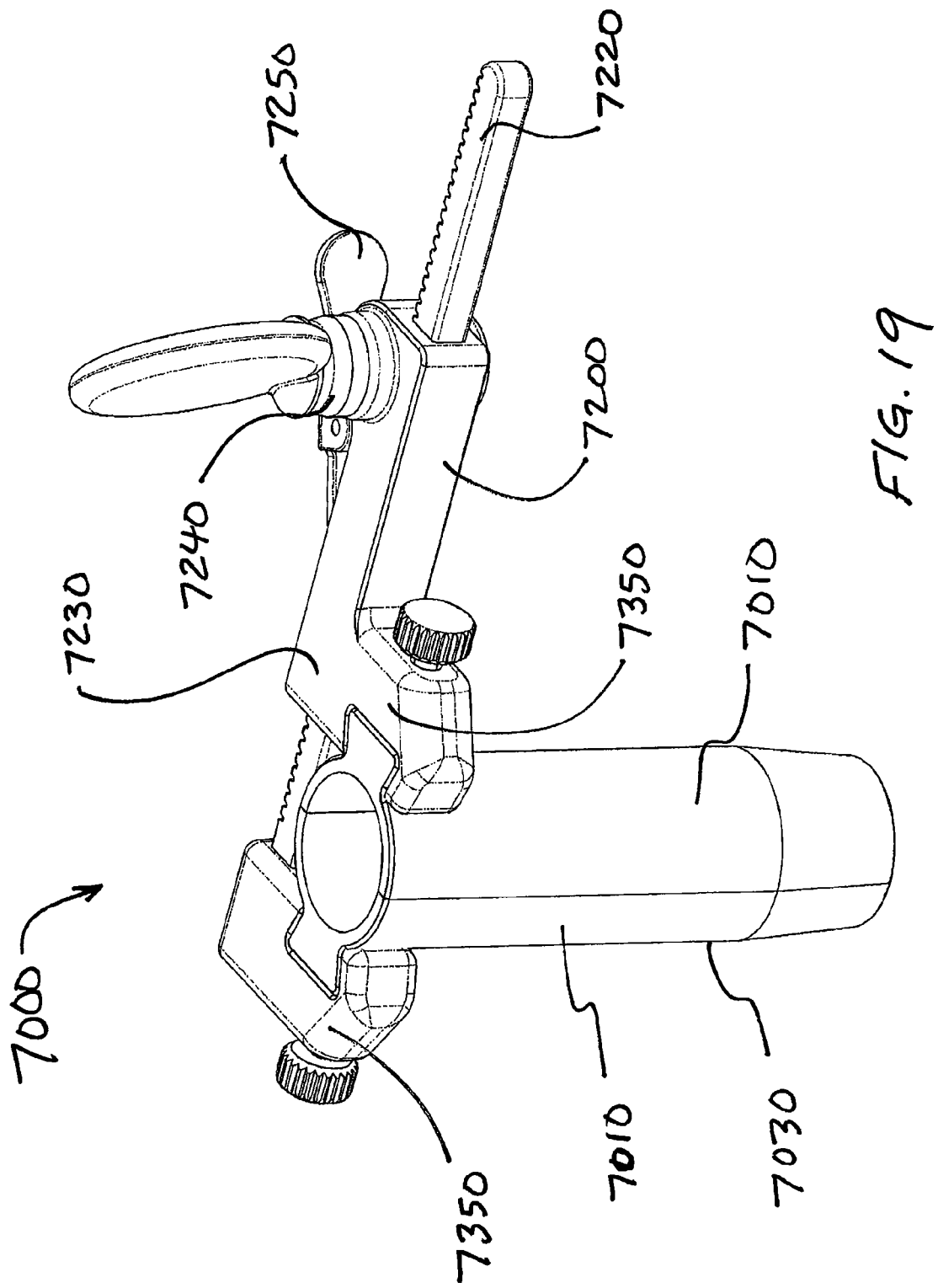
FIG. 19 is a perspective view of a clamp retractor assembly in accordance with an exemplary embodiment of the invention.
Figure 20:
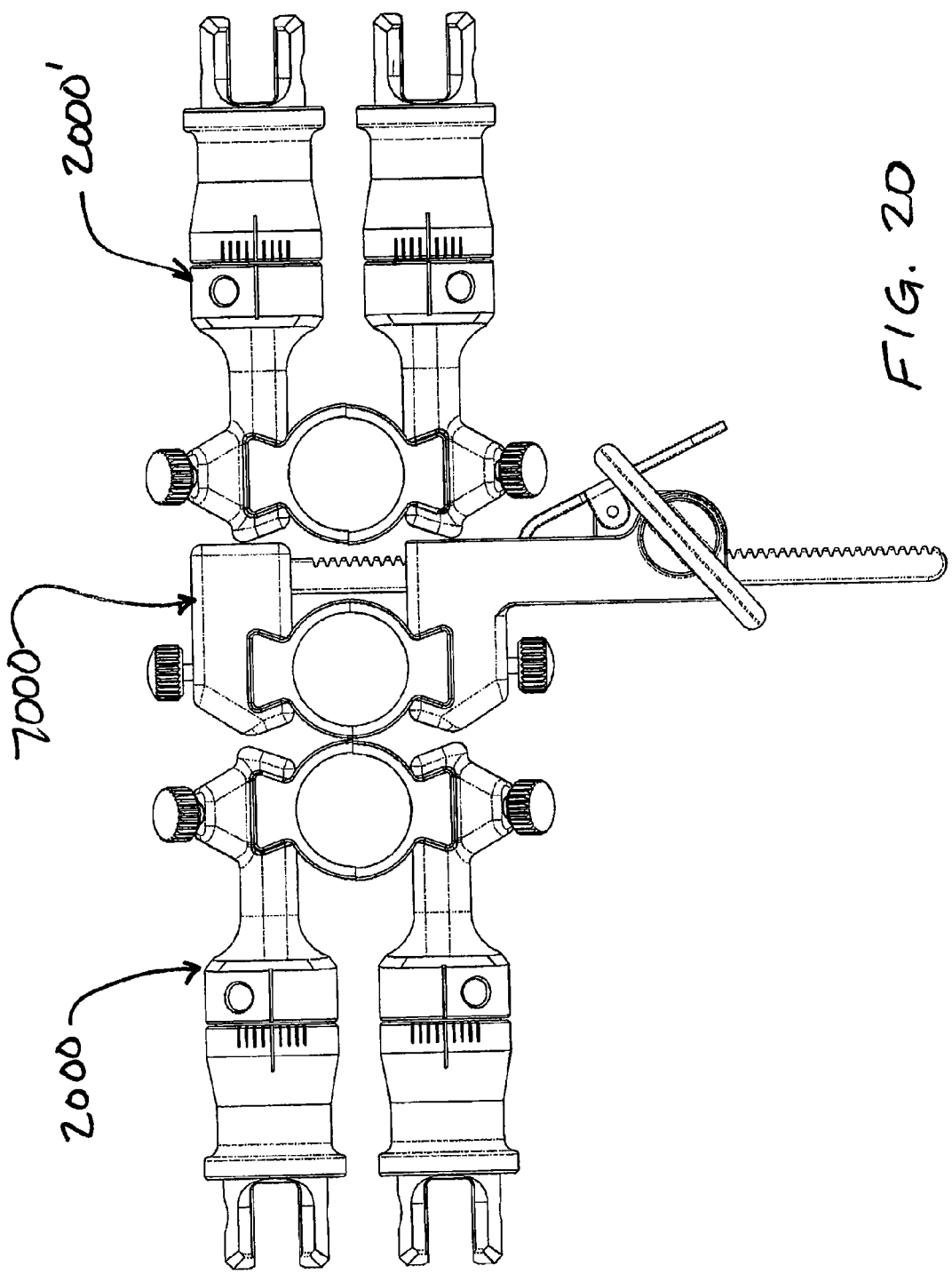
FIG. 20 is a top view of the retractor assemblies of FIG. 16 arranged with the clamp retractor assembly of FIG. 19.

In some instances, more than two percutaneous retractors may be desired, as in the situation where three pedicle screws are implanted in series at adjacent levels. For such instances, a third percutaneous retractor may be inserted between the two percutaneous retractors that are arranged end to end. FIGS. 19 and 20 illustrate a percutaneous clamp retractor 7000 for insertion between percutaneous retractors 2000 and 2000'. Clamp retractor 7000 includes a pair of semi-cylindrical retractor blades 7010. Blades 7010 mate with one another to form a cylindrical access portal 7300. Clamp retractor 7000 includes an adjustable clamp body 7200 having a rack 7220 and a translation assembly 7230. Rack 7220 and translation assembly 7230 each have a blade support 7350 that holds one of the blades 7010. Translation assembly 7230 includes a gear 7240 having a twist handle portion that is visible in the figures. Gear 7230 engages rack 7220 and is operable to adjust the distance between blades supports 7350, and consequently, blades 7010. A latch 7250 on lateral translation assembly engages rack 7220 to provide a locking mechanism to hold the relative positions of blades 7010. As seen in FIG. 20, the width of clamp retractor 7000 is very small. Blade supports 7350 are the widest sections of clamp retractor.

Figure 28:
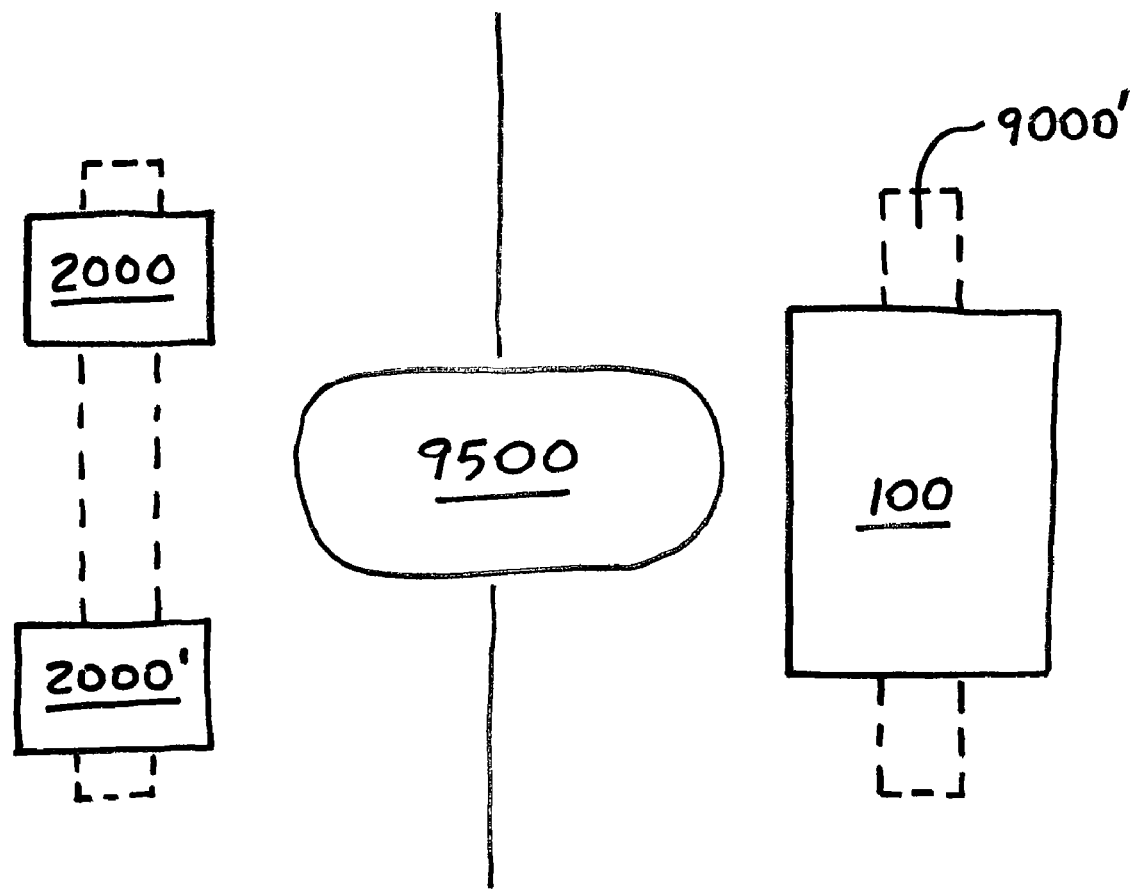
FIG. 28 is a schematic diagram illustrating one possible technique in accordance with the invention.

The mini-retractor assembly 100 and percutaneous retractor assembly 2000 are not strictly intended to be alternatives to one another. In a preferred approach, a mini-retractor assembly 100 and two percutaneous retractor assemblies 2000 and 2000' are used together in a procedure. For example, a common procedure requires implantation of two spinal rods at the same level, on different sides of the spine. Two percutaneous retractor assemblies 2000 and 2000' may be used on one side of the spine to open two small incisions, allowing insertion of two rod anchors and a first rod 9000. A single mini-open retractor assembly 100 may be used on the other side to open a single larger incision. The larger incision would not only allow insertion of two rod anchors and a second rod 9000', but also permit insertion of a cage or interbody 9500, which would be inserted prior to the inserting the second rod. A schematic diagram of this approach is shown in FIG. 28.

Figure 21:
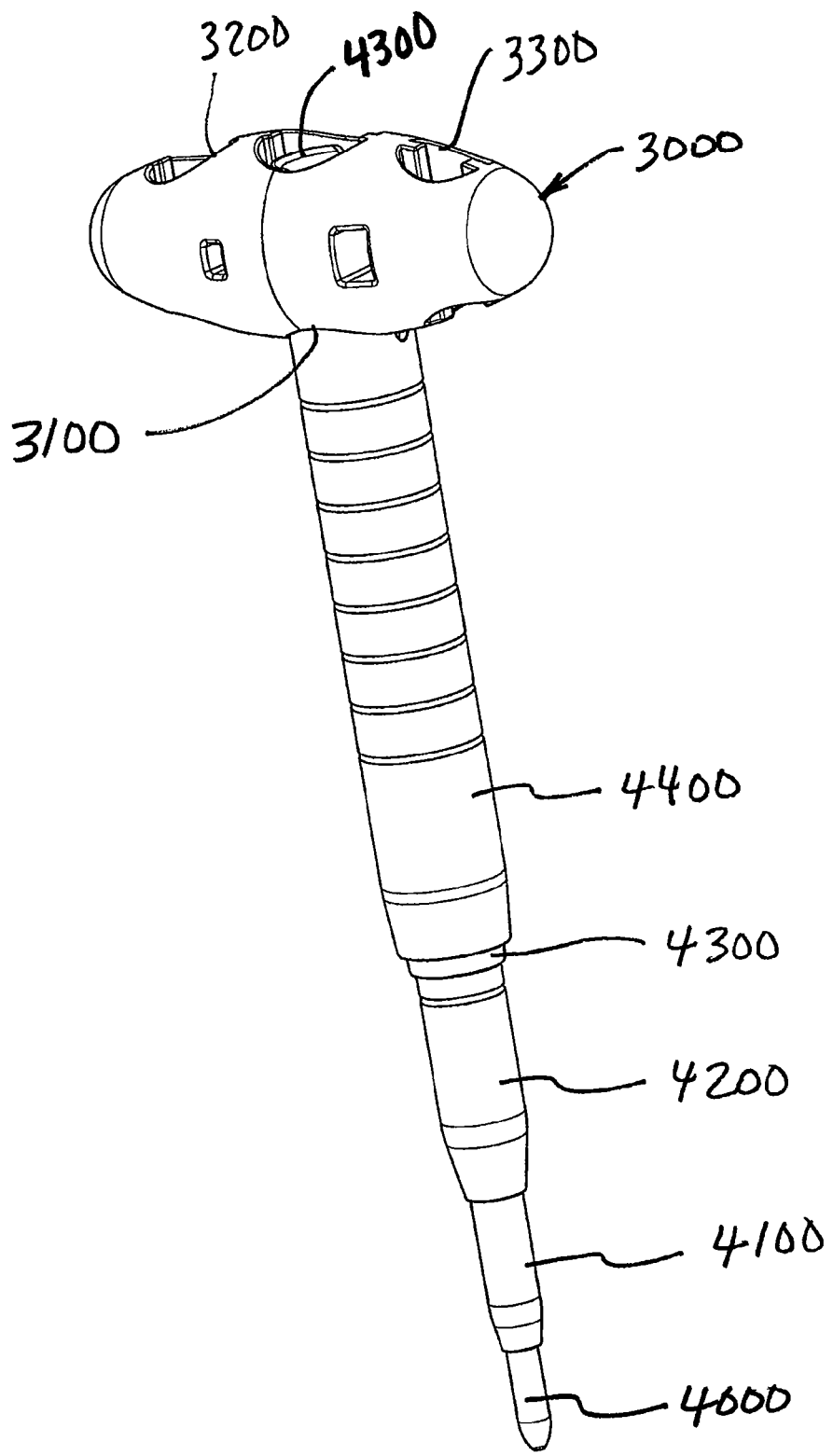
FIG. 21 is a first perspective view of components used for dilating an incision in accordance with an exemplary embodiment of the invention.
Figure 22:
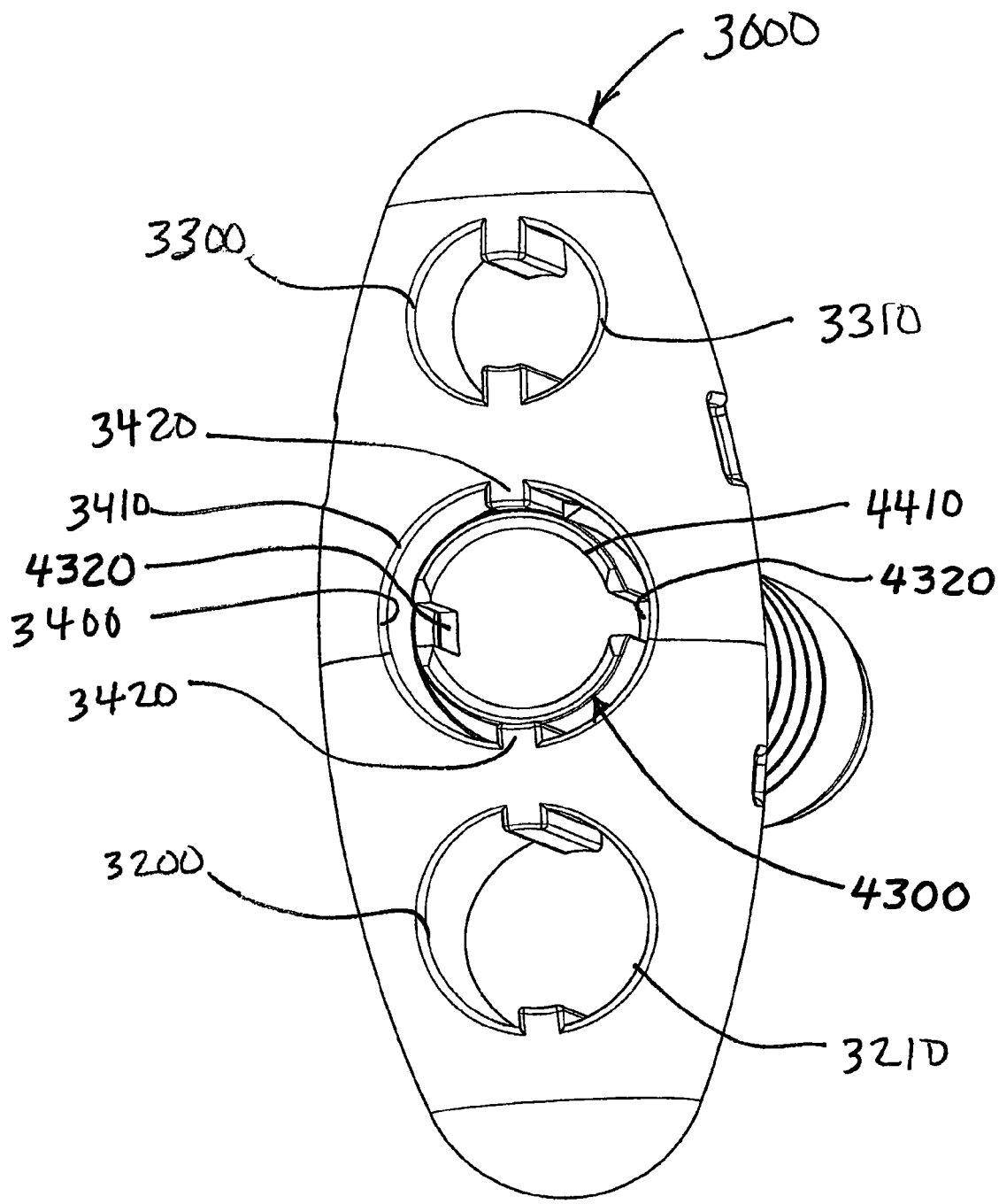
FIG. 22 is a second perspective view of the components of FIG. 21.

Various components may be used for dilating incisions in accordance with the techniques of the present invention. In a preferred technique, dilation tubes of different sizes are inserted over guidewires and removed from guidewires with a single tool. Referring to FIGS. 21 and 22, a dilator gripping tool 3000 is shown with a plurality of dilator tubes and a guidewire 4000. Gripping tool 3000 is made of a resilient flexible material that can flex and return to its original shape. Guidewire 4000 is circumscribed by a first dilator 4100, which is circumscribed by a second dilator 4200, which is circumscribed by a third dilator 4300, which is circumscribed by a fourth dilator 4400. Fourth dilator 4400 is received in a socket 3400 in gripping tool 3000. Socket 3400 extends through gripping tool 3000, forming a passage. Socket 3400 forms a pair of generally circular openings 3410 on the exterior of gripping tool 3000. Each opening 3410 includes a pair of diametrically opposed tabs 3420. Third dilator 4300 has a circular body 4310 with a pair of diametrically opposed notches 4320. Tabs 3120 have a spacing that corresponds to the outer diameter of dilator 4300.

Gripping tool 3000 includes two other sockets 3200 and 3300 configured like socket 3400, but with smaller dimensions. Socket 3200 forms circular openings 3210 having a diameter smaller than the diameter of openings 3410. Likewise, socket 3300 forms circular openings 3310 having a diameter smaller than the diameter of openings 3210. In this arrangement, gripping tool 3000 provides a universal tool for inserting and removing all of the dilators.

The dilator openings and diametrically opposed tabs provide an efficient way to advance one dilator into an incision and in the same motion or maneuver, to remove another dilator from the incision. Each dilator has a pair of notches at the top, such as notches 4320, that receive tabs in one of the openings in gripping tool. The tabs fit into the notches and help advance or push the dilator down into the incision. The dilator is advanced down over a smaller dilator, which would be dilator 4300 in FIG. 22. As the tabs advance downwardly, they surround the circumference of the smaller dilator in a snug friction fit. The tabs loosely fit in the notches of the larger dilator, however. Therefore, when the gripping tool is lifted upwardly, the tabs slide out of the larger dilator that was just inserted, but remain frictionally engaged around the smaller dilator. Consequently, the gripping tool can be lifted to release the larger dilator and in the same motion lift and remove the smaller dilator from the incision. This economy of motion can greatly reduce the amount of time and effort required to dilate an incision when using a number of different sized dilators in sequence.

Thus far, the retractor units 200, 300, 2000 and 2000' have been shown as having separate support mechanisms or support assemblies. The retractor units of the present invention may also be supported on a single support mechanism, however. That is, the "support assembly" referred to for retractor unit 200 and "support mechanism" referred to for retractor unit 300 may be parts of the same single component. For example, retractor units 200 and 300 may both be supported on a single support mechanism that features two rack segments joined at their ends in an L-shape.

Figure 23:
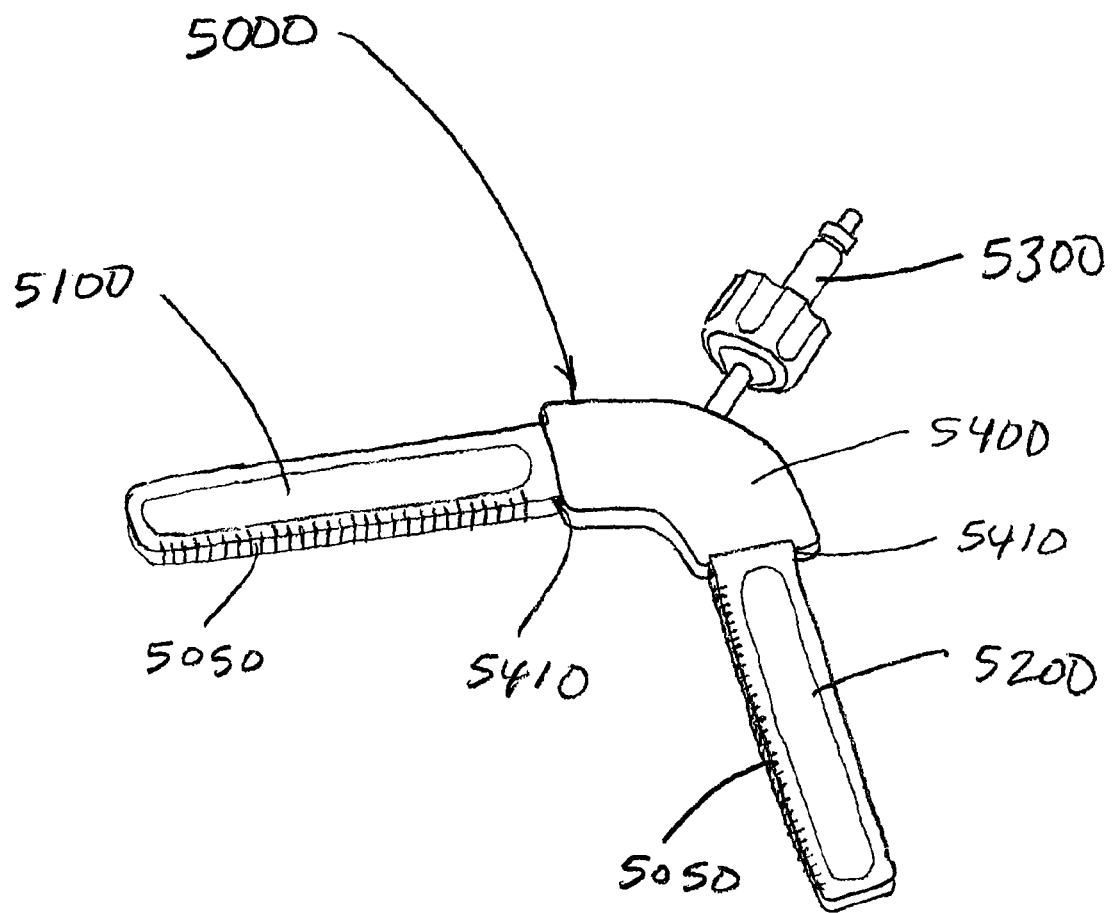
FIG. 23 is a perspective view of a support mechanism in accordance with an exemplary embodiment of the invention.

Referring to FIG. 23, an L-shaped support mechanism 5000 includes a first rack 5100 joined to a second rack 5200 at ninety degree angle. Racks 5100 and 5100 are configured to support stackable retractor units in a perpendicular nested arrangement, much like racks 218 and 318 in FIG. 1. In a preferred embodiment, racks 5100 and 5200 are detachably connected to a connector body, such as block 5400. Block 5400 includes slots 5410 that receive an end of each rack. In this configuration, racks can either be separately used, as shown in FIG. 1, or connected together as shown in FIG. 23, depending on the surgeon's preference. Because racks 5100 and 5200 lie in the same plane, retractor arms that are used with support mechanism 5000 may have slightly different contours than those shown on retractor units 200 and 300 to offset the arms and allow them to nest. Each rack 5100 and 5200 has teeth 5050 configured to engage a lateral adjustment assembly associated with a retractor arm. Support mechanism 5000 preferably includes an attachment, such as attachment 5300, to connect with a holding arm or other fixture connected to the operating table. A single support mechanism such as support mechanism 5300 may be preferable to provide more stability, and to maintain a generally perpendicular relationship between the nested retractor arms.

The retractor units of the present invention may include connectors and other features to enable the addition of optional components. For example, each retractor unit may include a hole, clip, clamp, slot or other mounting mechanism for a light source. In FIG. 1, for example, rack 318 includes a threaded hole 301 that allows a small light source to be screwed onto the rack. The mounting mechanism may be placed as shown in FIG. 1 or at various locations on the retractor unit to position the light source over an incision.

Applicants tested various components and instrumentation in accordance with the invention. In one test, a posterior stabilization procedure was performed on a cadaver using a percutaneous method at the L4/L5 level. Insertion points were selected on two pedicles by inserting needles under fluoroscopic imaging. Guidewires were then inserted through the needles and driven into the pedicles using a slide hammer. A small skin incision between about 1.5 mm to 2.0 mm in length was made at the location of each guidewire, which is done to reduce the potential for overstretching of the tissue and visible scarring from dilation. The needles were removed, leaving the guidewires in place. A 6 mm dilator was then placed over each guidewire to dilate the incision opening. The 6 mm dilator was then removed and replaced by a 10 mm dilator, which was removed and replaced by a 16.5 mm dilator.

After dilation was complete, a percutaneous retractor unit with semi-cylindrical retractor blades was prepared for placement over the 16.5 mm dilator. The retractor blades were moved together using lateral adjustment knobs so that the blades formed a cylindrical tube. The tube was lowered down over the dilator, and the round blades were inserted into the incision around the dilator. The retractor unit was then rested in a stable position on the cadaver. The size of the opening inside the retractor blades was approximately 16.5 mm. Once the retractor unit was resting in a stable position, the blades were spread apart to slightly widen the incision opening.

Next, a measuring instrument was inserted into the incision and viewed under imaging to determine the proper length for a pedicle screw. The pedicle screw with the proper length was then selected from a set, inserted down over the guidewire, and driven into the pedicle. The guidewire was removed, and final driving of the pedicle screw was completed.

The preceding steps were done for both incisions, so that both incisions contained a pedicle screw. The pedicle screws included polyaxial head components having channels adapted to receive a spinal fixation rod. Prior to inserting the rod, the heads were each oriented to face each other using manipulator instruments. After the screw heads were oriented, a length measurement was taken between the screw heads to determine the correct rod length.

The proper rod length was selected corresponding to the measured rod length, and a rod insertion instrument having many of the features of rod inserter 8000 was clamped to an end of the rod. The blades associated with the first retractor unit were retracted slightly apart to create a gap between the blades, the gap having a width slightly greater than the diameter of the rod. The blades on the second retractor unit were also retracted slightly to increase visibility of the screw in that incision. Using the rod inserter, the rod was fed through the blades of one of the retractor units and into the incision (the "first incision"). While being advanced into the first incision, the rod was generally parallel to the retractor blades to fit through the first incision opening. After the leading end of the rod was beneath the first incision, the rod was turned toward the adjacent incision (the "second incision") with the assistance of fluoroscopic imaging. Once turned, the leading end of the rod was advanced through the muscle tissue toward the pedicle screw beneath the second incision. The leading end was then passed into the channel of the pedicle screw, and the trailing end was placed into the pedicle screw beneath the first incision. Fasteners were inserted over the rod and into each pedicle screw head to anchor the rod in place. The slightly opened retractor blades in each retractor unit provided good visibility and assisted with navigating and titling drivers and counter torque instruments used to secure the fasteners. The instruments were removed from the first and second incisions, and the incisions were closed. The incision lines were approximately 20 mm in length at the conclusion of the procedure.

Referring to FIG. 27, a minimally invasive method 10000 for implanting an elongated spinal rod is illustrated in accordance with one exemplary method of the invention. The method may incorporate many of the steps described in the test procedure summarized above, or variations may be made. In step 10100, a first and a second incision is made. After dilation of each incision is completed, the guidewires and final dilator tubes are left in place in each incision. In step 10200, a first percutaneous retractor unit with semi-cylindrical retractor blades is lowered down over the dilator in the first incision, and the retractor blades are inserted into the first incision. The first retractor is then rested in a stable position on the patient. In step 10300, a first pedicle screw is advanced through the first retractor unit blades and driven into the pedicle beneath the first incision.

In step 10400, a second percutaneous retractor unit with semi-cylindrical retractor blades is lowered down over the dilator in the second incision, and the retractor blades are inserted into the second incision. The second retractor is then rested in a stable position on the patient. The second percutaneous retractor may be arranged end to end in a mirror arrangement with the first retractor. In step 10500, a second pedicle screw is advanced through the second retractor unit blades and driven into the pedicle beneath the second incision. The guidewires are removed from the incisions in step 10600, and additional tightening of the pedicle screws may be performed.

In step 10700, a rod is attached to a rod insertion instrument and advanced into the first incision. As in the test procedure described above, this step may be preceded by various steps to orient the screw heads and measure the precise rod length. After the leading end of the rod is beneath the first incision and above the first pedicle screw, the rod is turned subcutaneously in the slot between the retracted blades of the mini-retractor toward the second pedicle screw in step 10800. In step 10900, the leading end of the rod is advanced toward the second pedicle screw until it is received by the pedicle screw head. The trailing end of the rod is placed into the first pedicle screw in step 11000. After the rod ends are properly positioned in the pedicle screws, the rod is secured in the pedicle screws with fasteners in step 11100.

While preferred embodiments of the invention have been shown and described herein, it will be understood that such embodiments are provided by way of example only. Numerous variations, changes and substitutions will occur to those skilled in the art without departing from the spirit of the invention. In the method described above, for example, a number of additional steps and variations may be employed. For example, in one method according to the invention, the procedure may include inserting anchors into three or more incisions, and inserting a rod in the same manner as described above.

Accordingly, it is intended that the appended claims cover all such variations as fall within the spirit and scope of the invention.

What is claimed:

1. A tissue retractor system for maintaining and adjusting the size of an incision during a minimally invasive surgical procedure, the tissue retractor system comprising:
   a first arm extending from a support assembly, the first arm comprising a proximal span connected to the support assembly, a distal span and a blade support between the proximal span and the distal span;
   a second arm extending from the support assembly, the second arm comprising a proximal span connected to the support assembly, a distal span and a blade support between the proximal span and the distal span;
   a third arm extending from a support mechanism, the third arm comprising a proximal span connected to the support mechanism, a distal span and a blade support between the proximal span and the distal span; and
   a fourth arm extending from the support mechanism, the fourth arm comprising a proximal span connected to the support mechanism, a distal span and the distal span,
   wherein the third and fourth arms extend generally perpendicularly to the first and second arms in a nested arrangement above the first and second arms, with the third arm free to move laterally relative to the distal spans of the first and second arms in a direction generally parallel to the first and second arms, and with the fourth arm free to move laterally relative to the proximal spans of the first and second arms in a direction generally parallel to the first and second arms.

2. The tissue retractor system of claim 1, wherein the third and fourth arms each include an underside portion with recesses extending along the underside portion, the recesses receiving portions of the first and second arms.

3. The tissue retractor system of claim 2, wherein each of the underside portions has a convex curvature.

4. The tissue retractor system of claim 1, wherein the first, second, third and fourth arms intersect to form a generally rectangular opening.

5. The tissue retractor system of claim 4, wherein at least one blade support comprises a trapezoidal blade slot adjacent the rectangular opening, the blade slot having a short side adjacent the rectangular opening and a long side positioned away from the rectangular opening.

6. The tissue retractor system of claim 1, wherein the first and second arms each include a gliding surface on which the third and fourth arms rest, the gliding surface having a convex curvature.

7. The tissue retractor system of claim 1, wherein at least one of the first, second, third and fourth arms comprise a proximal end with a pivot hinge, and is pivotable through an angle of at least ninety degrees.

8. The tissue retractor system of claim 1, wherein at least one of the first, second, third and fourth arms includes a top-loading slot passing through said at least one of the first, second, third and fourth arms, the top-loading slot containing a retractor blade loaded into the slot from above the slot.

9. A tissue retractor system for maintaining and adjusting the size of an incision during a minimally invasive surgical procedure, the tissue retractor system comprising:
   a first arm extending from a support assembly, the first arm comprising a proximal span connected to the support assembly, a distal span, and a blade support between the proximal span and distal span;
   a second arm extending from the support assembly, the second arm comprising a proximal span connected to the support assembly, a distal span, and a blade support between the proximal span and distal span;
   a third arm extending from a support mechanism, the third arm comprising a proximal span connected to the support mechanism, a distal span, and a blade support between the proximal span and distal span; and
   a fourth arm extending from the support mechanism, the fourth arm comprising a proximal span connected to the support mechanism, a distal span, and a blade support between the proximal span and distal span,
   wherein at least one of the proximal spans includes an in-line pivot mechanism, the in-line pivot mechanism including a cylindrical knob that is rotatable about a longitudinal axis of the knob to pivot the arm to which the knob is connected, and an internal lock inside the knob to fix the orientation of the arm to which the knob is connected after a rotation of the knob, and
   wherein the third and fourth arms extend generally perpendicularly to the first and second arms in a nested arrangement above the first and second arms, with the third arm free to move laterally relative to the distal spans of the first and second arms in a direction generally parallel to the first and second arms, and with the fourth arm free to move laterally relative to the proximal spans of the first and second arms in a direction generally parallel to the first and second arms.

10. The tissue retractor system of claim 9, wherein the third and fourth arms each include an underside portion with recesses extending along the underside portion, the recesses receiving portions of the first and second arms.

11. The tissue retractor system of claim 10, wherein each of the underside portions has a convex curvature.

12. The tissue retractor system of claim 9, wherein the first, second, third and fourth arms intersect to form a generally rectangular opening.

13. The tissue retractor system of claim 12, wherein at least on of the first, second, third and fourth arms comprise a proximal end with a pivot hinge, and is pivotable through an angle of at least ninety degrees.

14. The tissue retractor system of claim 12, wherein at least one blade support comprises a trapezoidal blade slot adjacent the rectangular opening, the blade slot having a short side adjacent the rectangular opening and a long side positioned away from the rectangular opening.

15. The tissue retractor system of claim 9, wherein the support assembly includes a first lateral adjustment assembly connected with the first arm, the first lateral adjustment assembly operable to move the first arm relative to the second arm.

16. The tissue retractor system of claim 15, wherein the support assembly includes a second lateral adjustment assembly connected with the second arm, the second lateral adjustment assembly operable to move the second arm relative to the first arm, the first and second lateral adjustment assemblies being independently operable.

17. The tissue retractor system of claim 9, wherein the first and second arms each include a gliding surface on which the third and fourth arms rest, the gliding surface having a convex curvature.

18. A tissue retractor system for maintaining and adjusting the size of an incision during a minimally invasive surgical procedure, the tissue retractor system comprising:
   a first arm extending from a support assembly, the first arm comprising a proximal span connected to the support assembly, a distal span and a blade support between the proximal span and the distal span;

a second arm extending from the support assembly, the second arm comprising a proximal span connected to the support assembly, a distal span and a blade support between the proximal span and the distal span;

a third arm extending from a support mechanism, the third arm comprising a proximal span connected to the support mechanism, a distal span and a blade support between the proximal span and the distal span; and a fourth arm extending from the support mechanism, the fourth arm comprising a proximal span connected to the support mechanism, a distal span and a blade support between the proximal span and the distal span, wherein the third and fourth arms extend generally perpendicularly to the first and second arms in a nested arrangement, above the first and second arms with the third arm free to move laterally relative to the distal spans of the first and second arms in a direction generally parallel to the first and second arms, and with the fourth arm free to move laterally relative to the proximal spans of the first and second arms in a direction generally parallel to the first and second arms, wherein the support assembly includes a first lateral adjustment assembly connected with the first arm, the first lateral adjustment assembly operable to move the first arm relative to the second arm, and wherein the support assembly includes a second lateral adjustment assembly connected with the second arm, the second lateral adjustment assembly operable to move the second arm relative to the first arm, the first and second lateral adjustment assemblies being independently operable.

* * * * *

UNITED STATES PATENT AND TRADEMARK OFFICE
CERTIFICATE OF CORRECTION

| | | |
|---|---|---|
| PATENT NO. | : 8,211,012 B2 | Page 1 of 1 |
| APPLICATION NO. | : 12/241897 | |
| DATED | : July 3, 2012 | |
| INVENTOR(S) | : Charles Wing et al. | |

It is certified that error appears in the above-identified patent and that said Letters Patent is hereby corrected as shown below:

In claim 13, column 20, line 40, "on of the first, second," should read --one of the first, second,--

Signed and Sealed this
Sixth Day of November, 2012

David J. Kappos
*Director of the United States Patent and Trademark Office*